(12) United States Patent
Balraj et al.

(10) Patent No.: US 10,202,617 B2
(45) Date of Patent: Feb. 12, 2019

(54) EXPRESSION CASSETTE FOR EFFICIENT SURFACE DISPLAY OF ANTIGENIC PROTEINS

(75) Inventors: Premanand Balraj, Singapore (SG); Hwei-Sing Jimmy Kwang, Singapore (SG); Anbu Kumar Karuppannan, Singapore (SG)

(73) Assignee: Temasek Life Sciences Laboratory Limited, Singapore (SG)

(*) Notice: Subject to any disclaimer, the term of this patent is extended or adjusted under 35 U.S.C. 154(b) by 0 days.

(21) Appl. No.: 13/983,722

(22) PCT Filed: Feb. 8, 2012

(86) PCT No.: PCT/SG2012/000035
§ 371 (c)(1),
(2), (4) Date: Nov. 14, 2013

(87) PCT Pub. No.: WO2012/108840
PCT Pub. Date: Aug. 16, 2012

(65) Prior Publication Data
US 2014/0127216 A1    May 8, 2014

Related U.S. Application Data

(60) Provisional application No. 61/462,878, filed on Feb. 8, 2011.

(51) Int. Cl.
*C12N 7/00* (2006.01)
*A61K 39/12* (2006.01)
(Continued)

(52) U.S. Cl.
CPC .............. *C12N 15/86* (2013.01); *C07K 16/08* (2013.01); *C07K 16/081* (2013.01); *C12N 7/00* (2013.01);
(Continued)

(58) Field of Classification Search
None
See application file for complete search history.

(56) References Cited

U.S. PATENT DOCUMENTS

| 5,162,222 A | * | 11/1992 | Guarino | ............... | C12N 9/6459 435/320.1 |
| 5,348,886 A | * | 9/1994 | Lee | ......................... | C12N 15/70 435/252.3 |

(Continued)

FOREIGN PATENT DOCUMENTS

| WO | WO 2005080417 A2 | * | 9/2005 |
| WO | WO 2009009215 A2 | * | 1/2009 |
| WO | WO 2010148511 A1 | * | 12/2010 |

OTHER PUBLICATIONS

Long et al., "Functional Role of the Cytoplasmic Tail Domain of the Major Envelope Fusion Protein of Group II Baculoviruses," Journal of Virology, vol. 80, No. 22: 11226-11234 (2006).*

(Continued)

*Primary Examiner* — Janet L Andres
*Assistant Examiner* — M Franco G Salvoza
(74) *Attorney, Agent, or Firm* — Schwegman Lundberg & Woessner, P.A.

(57) ABSTRACT

An expression cassette, wherein said expression cassette comprises: (a) an ie 1 promoter from white spot syndrome virus or a variant thereof; (b) a nucleic acid sequence encoding an N-terminal gp64 signal peptide or variant thereof, a nucleic acid sequence encoding an antigenic peptide, a nucleic acid encoding a transmembrane region, and a nucleic acid encoding a gp64 cytoplasmic region or variant thereof; in which the promoter is operably linked to the nucleic acid sequence.

29 Claims, 20 Drawing Sheets

Specification includes a Sequence Listing.

(51) Int. Cl.
*C12N 15/86* (2006.01)
*C07K 16/08* (2006.01)
*A61K 39/00* (2006.01)

(52) U.S. Cl.
CPC .......................... *A61K 2039/505* (2013.01); *A61K 2039/6068* (2013.01); *C07K 2317/76* (2013.01); *C07K 2319/00* (2013.01); *C07K 2319/03* (2013.01); *C07K 2319/035* (2013.01); *C12N 2710/10043* (2013.01); *C12N 2750/10022* (2013.01); *C12N 2750/10034* (2013.01); *C12N 2770/10022* (2013.01); *C12N 2770/10034* (2013.01); *C12N 2770/32122* (2013.01); *C12N 2770/32134* (2013.01); *Y02A 50/386* (2018.01); *Y02A 50/394* (2018.01); *Y02A 50/412* (2018.01); *Y02A 50/466* (2018.01)

(56) References Cited

U.S. PATENT DOCUMENTS

| | | | | |
|---|---|---|---|---|
| 7,429,480 | B2* | 9/2008 | Kou et al. | 435/320.1 |
| 7,527,967 | B2* | 5/2009 | Chao | C07K 14/005 424/211.1 |
| 8,513,006 | B2* | 8/2013 | Ross | A61K 39/145 424/202.1 |
| 2006/0216702 | A1* | 9/2006 | Compans et al. | 435/5 |
| 2008/0003203 | A1 | 1/2008 | Hu et al. | |
| 2009/0016992 | A1* | 1/2009 | Eichmeyer et al. | 424/93.2 |
| 2009/0017064 | A1* | 1/2009 | Wu | A61K 39/12 424/205.1 |
| 2010/0323398 | A1* | 12/2010 | Blissard | C07K 14/005 435/69.1 |

OTHER PUBLICATIONS

Marks et al., "Transcriptional analysis of the white spot syndrome virus major virion protein genes," Journal of General Virology 84: 1517-1523 (2003).*

Yin et al., "Self-assembly of virus-like particles of porcine circovirus type 2 capsid protein expressed from *Escherichia coli*," Virology Journal 7: 166 (2010).*

He et al., "Baculovirus vector as a delivery vehicle for influenza vaccines," Expert Rev Vaccines 8(4): 455-467 (2009).*

Prabakaran et al., "Gastrointestinal Delivery of Baculovirus Displaying Influenza Virus Hemagglutinin Protects Mice against Heterologous H5N1 Infection," Journal of Virology, vol. 84, No. 7: 3201-3209 (2010).*

He et al., "WSSV ie1 promoter is more efficient that CMV promoter to express H5 hemaglutinin from influenza virus in baculovirus as a chicken vaccine," BMC Microbiology 8:238 (2008).*

Prabakaran et al. "Gastrointestinal Delivery of Baculovirus Displaying Influenza Virus Hemagglutinin Protects Mice against Heterologous H5N1 Infection," Journal of Virology, vol. 84, No. 7: 3201-3209 (Year: 2010).*

He et al., "WSSV ie1 promoter is more efficient than CMV promoter to express H5 hemagglutinin from influenza virus in baculovirus as a chicken vaccine," BMC Microbiology 8:238 (Year: 2008).*

Fan et al., "Construction and immunogenicity of recombinant pseutodype baculovirus expressing the capsid protein of porcine circovirus type 2 in mice," Journal of Virological Methods 150: 21-26 (Year: 2008).*

"International Application No. PCT/SG2012/000035, International Search Report dated Mar. 28, 2012", (Mar. 28, 2012), 5 pgs.

"Chinese Application No. 201280016937.7, Office Action dated Apr. 20, 2015", (Apr. 20, 2015), 12 pgs.

"Chinese Application No. 201280016937.7, Office Action dated Aug. 12, 2014", (Aug. 12, 2014), 8 pgs.

Gao, Hui, et al., "Efficient gene delivery into mammalian cells mediated by a recombinant baculovirus containing a whispovirus ie1 promoter, a novel shuttle promoter between insect cells and mammalin cells", Journal of Biotechnology 131 (2007) 138-143, (2007), 138-143.

Hu, Yu-Chen, "Baculoviral vectors for gene delivery: a review", Current Gene Therapy (Impact Factor: 4.91). Mar. 2008; 8(1):54-65, (Mar. 2008), 54-65.

Lin, Yueh H., et al., "Baculovirus surface display of sC and sB proteins of avian reovirus and immunogenicity of the displayed proteins in a mouse model", Vaccine, vol. 26, Issue 50, Nov. 25, 2008, pp. 6361-6367, (Nov. 25, 2008), 6361-6367.

Meng, Tao, et al., "Display of VP1 on the Surface of Baculovirus and Its Immunogenicity against Heterologous Human Enterovirus 71 Strains in Mice", PLoS ONE 6(7): e21757, Jul. 1, 2011, (Jul. 1, 2011), 12 pgs.

Shen, Jia, et al., "The Advancement about Baculovirus Surface Display System", Microbiology, 35(3), 421-425, Mar. 20, 2008, (Mar. 20, 2008), 421-425.

Wang, Bao-Zhong, et al., "Incorporation of High Levels of Chimeric Human Immunodeficiency Virus Envelope Glycoproteins into Virus-Like Particles", J. Virol., 2007, vol. 81, No. 20, Aug. 1, 2007, 10869-10878, (Aug. 1, 2007), 10869-10878.

Xu, Xin-Gang, et al., "Baculovirus surface display of E envelope glycoprotein of Japanese encephalitis virus and its immunogenicity of the displayed proteins in mouse and swine models", Vaccine, vol. 29, Issue 4, 17 Jan. 2011, pp. 636-643, (Jan. 17, 2011), 636-643.

Yang, Ding-Gang, et al., "Avian Influenza Virus Hemagglutinin Display on Baculovirus Envelope: Cytoplasmic Domain Affects Virus Properties and Vaccine Potential", Molecular Therapy, vol. 15, No. 5, 989-996, May 2007, (May 2007), 989-996.

"Chinese Application No. 201280016937.7, Office Action dated Nov. 10, 2015", (w/ English Translation), 18 pgs.

"International Application No. PCT/SG2012/000035, International Preliminary Report on Patentability dated Aug. 13, 2013", 8 pgs.

"International Application No. PCT/SG2012/000035, Written Opinion dated Mar. 28, 2012", 7 pgs.

Shen, Jia, et al., "The Advancement about Baculovirus Surface Display System", *Microbiology*, 35(3), 421-425, (English Translation), (2008), 8 pgs.

Tami, C., et al., "Immunological properties of FMDV-gP64 fusion proteins expressed on SF9 cell and baculovirus surfaces", Vaccine, 23(6), (2004), 840-845.

* cited by examiner

Figure 3

← Vp1-N-ter

VP1c-ter

H3N2-HA-TMD
(27 aa)

GP64-c-ter
(6 aa)

Plasma membrane

SF9 II cells

Figure 8

Lanes; Capsid fragments;
1, 76 – 180; 2, 76 – 135; 3, 121 – 180

Anti rBacORF7

| ie1 Promoter | gp64 signal peptide | Antigenic peptide |

FIGURE 20A

| ie1 Promoter | gp64 signal peptide | Antigenic peptide | Transmembrane region |

FIGURE 20B

| ie1 Promoter | gp64 signal peptide | Antigenic peptide | Transmembrane region | gp64 cytoplasmic domain |

FIGURE 20C

EXPRESSION CASSETTE FOR EFFICIENT SURFACE DISPLAY OF ANTIGENIC PROTEINS

PRIORITY CLAIM TO RELATED APPLICATIONS

This application is a national stage application under 35 U.S.C. § 371 of PCT/SG2012/000035, filed Feb. 8, 2012, and published as WO 2012/108840 A1 on Aug. 16, 2012, which claims priority to U.S. Provisional Application No. 61/462,878, filed Feb. 8, 2011, which applications and publication are incorporated by reference as if reproduced herein and made a part hereof in their entirety, and the benefit of priority of each of which is claimed herein.

TECHNICAL FIELD

The present invention relates generally to biomolecule surface display systems, with particular application to display of antigenic peptides, for example viral proteins, for example viral capsid proteins to be used as vaccine. In particular, the present invention relates to methods, vaccines, immunological compositions and kits for treating and/or preventing viral infections, and to associated methods for modulating an immune response.

BACKGROUND ART

Several hundred different known viruses infect humans and animals. Viruses that infect humans and animals often spread via respiratory and enteric excretions. For example, enterovirus 71 (EV71) is a single stranded, RNA virus of the genus Enterovirus in the family Picornaviridae. It is classified genetically into 3 groups (A, B and C) and 11 genotypes (A, B1-B5, C1-C5). EV71 comprises four major capsid proteins such as VP1, VP2, VP3 and VP4. Of these, VP1 is thought to be mainly responsible for the attachment of virus to target cells and hence harbours the main antigenic determinant for virus neutralization. Indeed, immunological studies with different enterovirus strains have indicated that the dominant epitopes of several neutralizing mAbs are located on VP1. EV71 is one virus responsible for hand foot and mouth disease.

Hand foot and mouth disease has become a major emerging infectious disease and is an important threat especially in Asia. A large outbreak of HFMD due to EV71 infection occurred in Taiwan in 1998, including 129,106 case reports, 405 children with severe complications, and more than 80 deaths. Since 1997, EV71 infection has taken on new significance, with increasing numbers of cases. Episodes caused by various strains of EV71 have continued to reappear in other countries such as Thailand, China and Vietnam. The expanding geographic distribution of EV71 infections with recent outbreaks in Singapore indicates that more human populations are at risk. Conventional EV71 vaccines are based on inactivated viruses which are produced in cell lines and inactivated by chemical means. However, the virulent nature of the virus requires that the viruses be handled under biosafety level conditions, thus the production of vaccines candidates using conventional techniques would require significant changes in current manufacturing procedures that might delay vaccine production in case of the outbreak.

Formalin-inactivated and live attenuated vaccines in controlling epidemic poliomyelitis and in the eradication of poliovirus highlights the potential for control of EV71 epidemics by mass vaccination. Based on this formalin-inactivated EV71 vaccine was developed in response to Bulgarian epidemic in 1975 but was not used to control the epidemic and has not been used since. Furthermore no data on the efficacy of the Bulgarian vaccine are available.

A good vaccine effective for protection against viral infections, such as EV71 is therefore highly desirable.

SUMMARY OF THE INVENTION

In a first aspect there is provided an expression cassette, wherein said expression cassette comprises:
(a) an ie1 promoter from white spot syndrome virus or a truncated sequence thereof;
(b) a nucleic acid sequence encoding an N-terminal gp64 signal peptide or variant thereof, a nucleic acid sequence encoding an antigenic peptide, a nucleic acid encoding a transmembrane region, and a nucleic acid encoding a gp64 cytoplasmic region or variant thereof;
in which the promoter is operably linked to the nucleic acid sequence.

In a second aspect there is provided an expression vector comprising an expression cassette as described herein.

In a third aspect there is provided a kit comprising the expression cassette as described herein or an expression vector as described herein and packaging materials therefor.

In a fourth aspect there is provided a host cell comprising an expression cassette as described herein or an expression vector as described herein.

In a fifth aspect there is provided an immunogenic composition comprising an expression cassette as described herein, an expression vector as described herein, or a host cell as described herein, together with a pharmaceutically acceptable carrier, adjuvant, diluent or excipient.

In a sixth aspect there is provided a vaccine comprising an expression cassette as described herein, an expression vector as described herein or a host cell as described herein, together with a pharmaceutically acceptable carrier, adjuvant, diluent or excipient.

In a seventh aspect, there is provided an antibody produced by an organism inoculated with a vaccine according to the present invention.

In an eight aspect, there is provided an anti-serum containing an antibody of the present invention.

In a ninth aspect there is provided an expression cassette as described herein, an expression vector as described herein, a host cell as described herein, an immunogenic composition as described herein, a vaccine as described herein, an antibody as described herein or an anti-serum as described herein for use in the treatment or prevention of a disease in a subject, in which the antigenic peptide is expressed by said expression vector in said subject.

In a tenth aspect there is provided a method for modulating an immune response, wherein said method comprises administering to a subject an effective amount of an expression cassette as described herein, an expression vector as described herein, a host cell as described herein, an immunogenic composition as described herein, a vaccine as described herein, an antibody as described herein, or an anti-serum as described herein.

In an eleventh aspect there is provided a use of an expression cassette as described herein, an expression vector as described herein, a host cell as described herein, an immunogenic composition as described herein, a vaccine as described herein, an antibody as described herein, or an anti-serum as described herein in the manufacture of a medicament for the modulation of an immune response in a subject.

In a tenth aspect there is provided a method for presenting, producing or displaying an antigenic peptide, wherein the method comprises:

(a) inserting a nucleic acid encoding the polypeptide into an expression vector as described herein;

(b) transfecting at least one host cell with the expression vector; and (c) expressing the polypeptide from the expression vector wherein the polypeptide is presented or displayed on the surface membrane of a baculovirus.

In a tenth aspect there is provided an antigenic peptide obtained by a method as described herein.

In an eleventh aspect there is provided a method of diagnosis comprising use of an antigenic peptide as described herein.

BRIEF DESCRIPTION OF THE FIGURES

The present invention will now be described, by way of example only, with reference to the following figures.

FIG. 3. Surface display pattern of rVP1 protein on the SF-9 II cell plasma membrane. FIG. 3 illustrates that the GP64 C-terminal part of the protein is located inside the SF-9 II cell while the H3N2 transmembrane domain as well as the antigenic peptide are located in the extracellular medium.

FIG. 4 clearly shows that rVP1 is localized at the plasma membrane, thus demonstrating the anchoring of rVP1 on the surface of the Sf-9 cells. For more details please see example 1.

rBac-VP1[1]—recombinant baculovirus encoding the novel "expression cassette".

rBac-VP1[2]—recombinant baculovirus encoding the expression cassette with full length gp64 as fusion partners.

Figure 5:
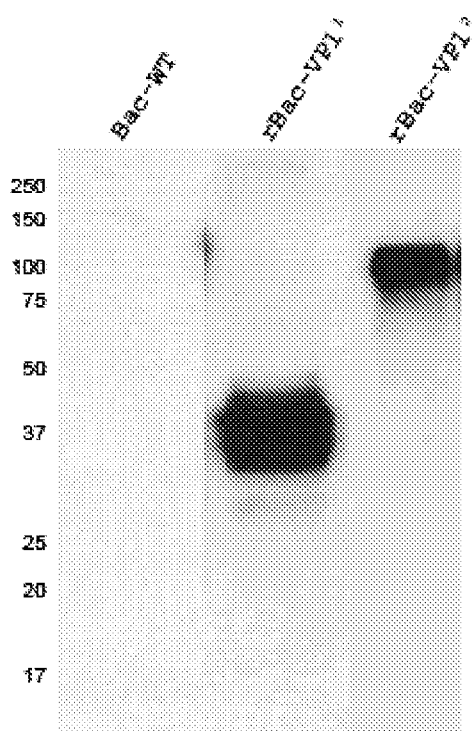
FIG. 5. Confirmation of the expression of rVP1 of EV71 on the Bac-VP1 envelope. The cells were infected at a MOI of 10 and harvested 3 days post-infection. The supernatant was collected and subjected to a western blotting assay using anti-VP1 (guinea pig) polyclonal antibodies followed by anti-guinea pig HRP labeled secondary antibody.

As can be seen from FIG. 5, no proteins were detected in the Baculovirus-WT (wild type). In comparison, clear bands were seen from the supernatants obtained from cells infected with rBac-Vp1[1] and rBac-Vp1[2], indicating that rVP1 was successfully expressed on the Bac-VP1 virus envelope.

Figure 6:
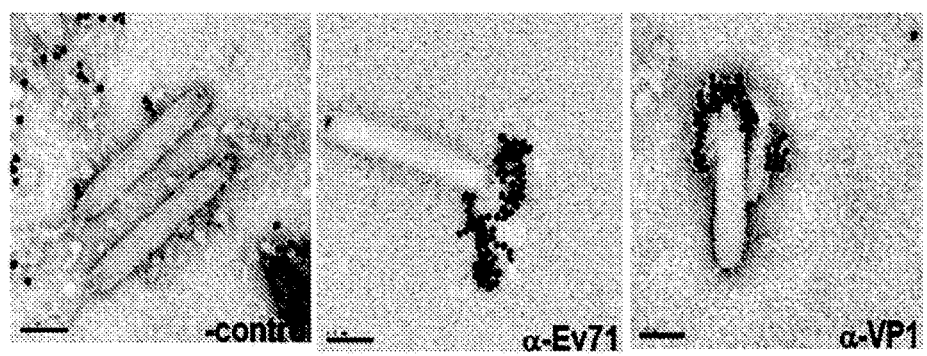

FIG. 6. Immunogold electron micrographs of purified baculoviruses detected by anti-EV71 and anti-VP1 antibodies as the primary antibodies and anti-mouse IgG conjugated with 5-nm gold particles as the secondary antibody (magnification 200,000×, scale bar=100 nm). The gold particles (shown as black spots) indicate the location of EV71 and VP1 protein expression. No gold particles were displayed on the surface of baculovirus-WT (control) whereas EV71 and VP1 were detected on the surface of the recombinant baculoviruses of the present invention.

Figure 7:
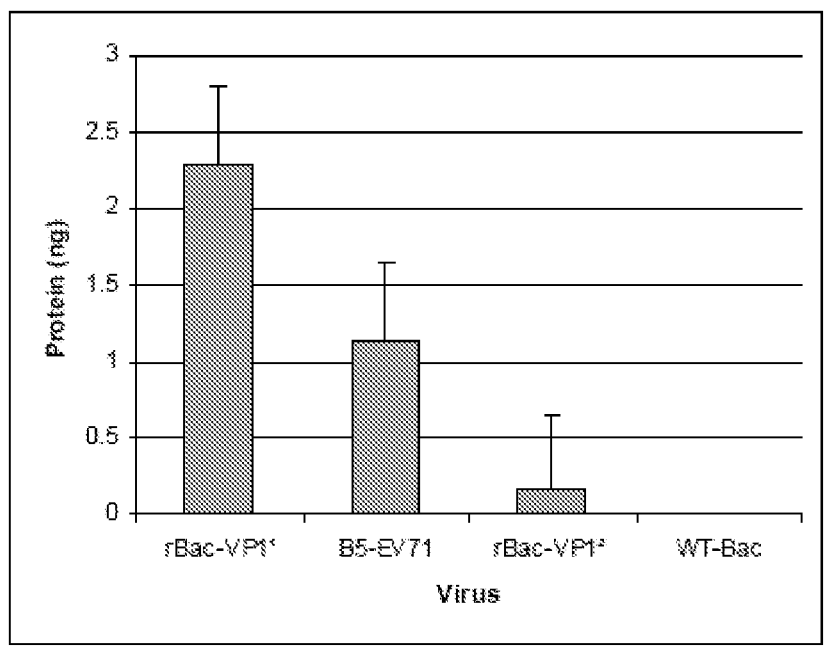

FIG. 7. Quantification of rVP1 of EV71 displayed on the envelope of recombinant baculovirus. The displayed rVP1 proteins on baculovirus envelope were probed using anti-VP1 monoclonal antibodies. The amount of VP1 on the rBac-VP1 ($10^7$/ml), rBac-VP1[2] ($10^7$/ml), EV71 WT (B5 strain) ($10^7$/ml), WT baculovirus was calibrated to the amount of purified recombinant VP1 protein. The band intensities on the Western blot, were scanned and analysed using ODYSSEY LICOR fluorescence scanner and software. The data were the mean of three independent experiments.

rBac-VP1[1]—recombinant baculovirus encoding the novel "expression cassette"

rBac-VP1[2]—recombinant baculovirus encoding the expression cassette with full length gp64 as fusion partners.

FIG. 7 shows that rBac-VP1[1] (novel expression cassette) has the highest expression of VP1 protein compared to B5-Ev71 and rBac-VP1[2] (full length gp64), thus demonstrating the usefulness of the novel expression cassette for producing large amounts of VP1 antigenic peptide.

Figure 8:
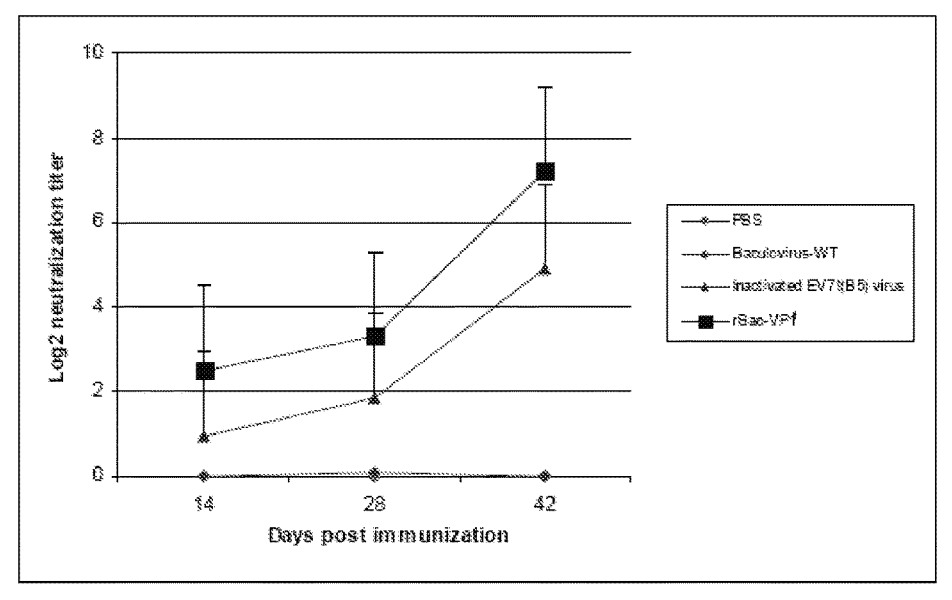

FIG. 8. Ability of test sera to neutralize virus infectivity. *50 µA of virus suspension containing 100TCID$_{50}$ EV71 virus was pre-incubated with 50 µl of serial two-fold dilutions of antibodies for 30 min before adding to RD cells in 96-well plates. After 3 days at 37° C., the titer of neutralizing antibody was read as the highest dilution that gave complete protection from CPE.

As can be seen from FIG. 8, rBac-VP1 resulted in a higher neutralization titer compared to inactivated EV71 (B5) virus. The negative controls PBS and Baculovirus-WT (results are overlapping, Baculovirus-WT results are superimposed over PBS results) showed a negligible neutralization titer as expected.

Figure 9:
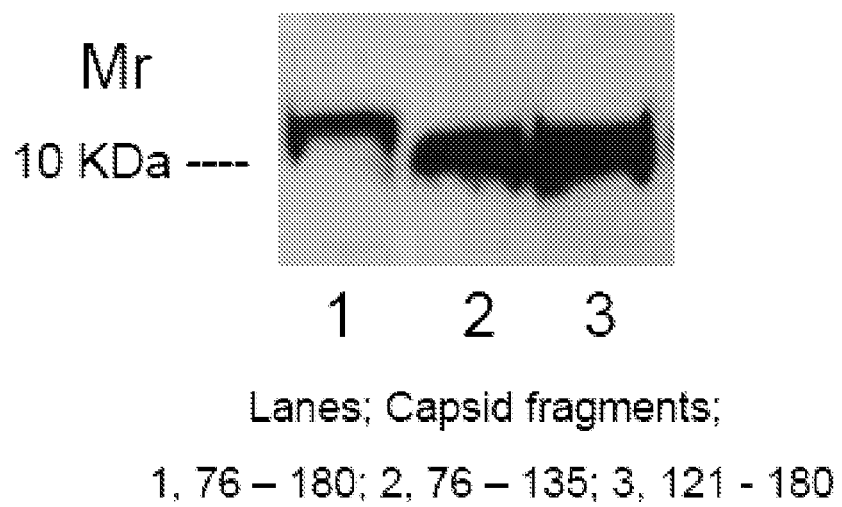

FIG. 9. Western blot of sucrose gradient purified Baculovirus with surface displayed capsid regions of PCV2 capsid (rBac-PCV2) using 8C2 (anti ORF2) monoclonal antibody (primary) followed by anti-mouse HRP labelled secondary antibody.

As can been seen from FIG. 9, abundant expression levels of each of the capsid protein regions was present in the purified baculovirus.

Figure 10:
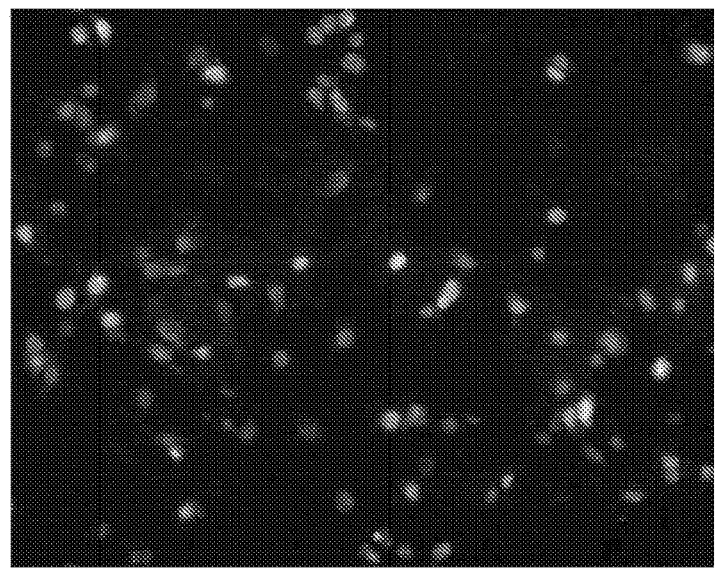

FIG. 10. Immunofluorescence assay of PK-15 cells infected with PCV2 using antibodies from Guinea pig immunized with purified rBac-PCV2 and Alexa Fluor 546 labelled anti-guinea pig secondary antibodies (magnification ×40). Light grey portions of FIG. 10 indicate Alexa Fluor 546 staining. FIG. 10 therefore shows good expression of PCV2 protein in cells infected with PCV2.

Figure 11:
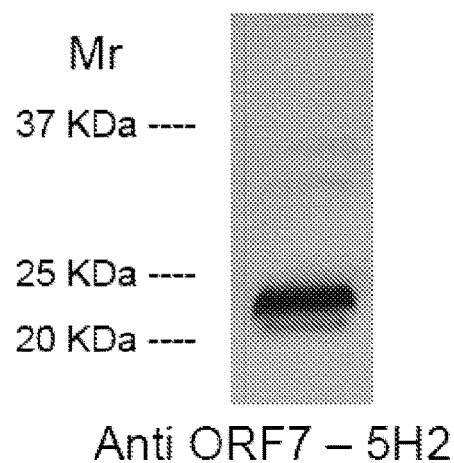

FIG. 11. Western blot of sucrose gradient purified rBac-ORF7 proteins of PRRSV using 5H2 (ORF7) monoclonal antibodies (primary) followed by anti-mouse HRP labeled secondary antibodies.

FIG. 11 clearly shows that there is abundant expression of the ORF7 protein of PRRSV.

Figure 12:
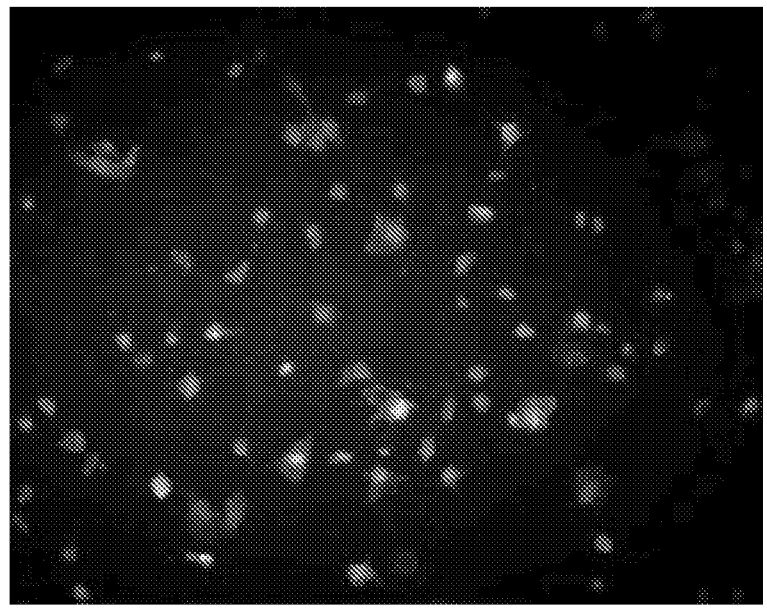

FIG. 12. Immunofluorescence assay of MARC-145 cells infected with PRRSV using antibodies from Guinea pig immunized with purified rBac-ORF7 proteins, followed by Alexa fluor 546 labelled anti-guinea pig secondary antibodies (magnification ×40). Light grey portions of FIG. 11 indicate Alexa Fluor 546 staining. FIG. 11 therefore shows good expression of ORF protein in cells infected with PRRSV.

Figure 13:
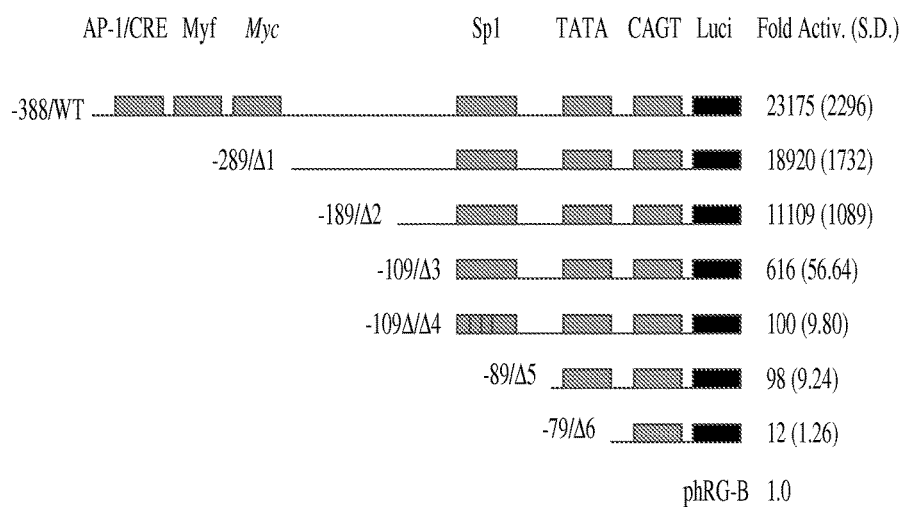

FIG. 13. Schematic diagram of cis-elements in the ie1 promoter of White Spot Syndrome Virus (WSSV).

Figure 14:
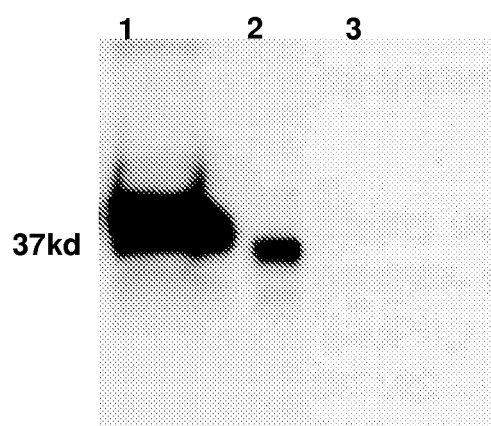

FIG. 14. Western blot analysis of baculovirus anchored nucleocapsid alpha protein. Bac-noda, Betanodavirus and wild type baculovirus were subjected to western blot using anti-noda capsid polyclonal antibody (guinea pig) and the respective secondary HRP conjugated antibody. (1) Bac-Noda, (2) Betanodavirus, (3) Wild type baculovirus.

As can be seen from FIG. 14, no proteins were detected in the Baculovirus-WT (wild type). In comparison, clear bands were seen from the supernatants obtained from cells infected with rBac-Vp1$^1$ and rBac-Vp1$^2$, indicating that rVP1 was successfully expressed on the Bac-VP1 virus envelope.

Figure 15:
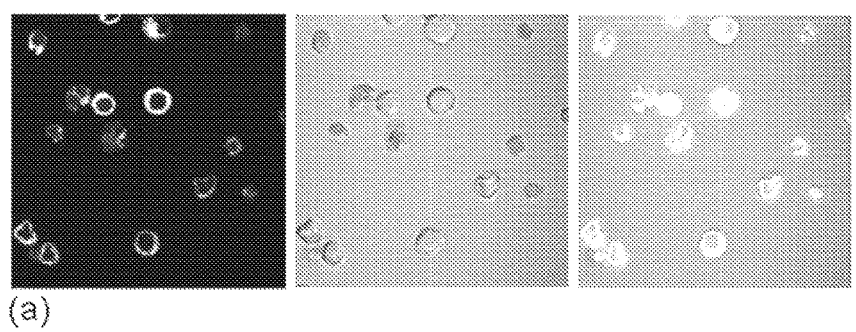
Figure 15:
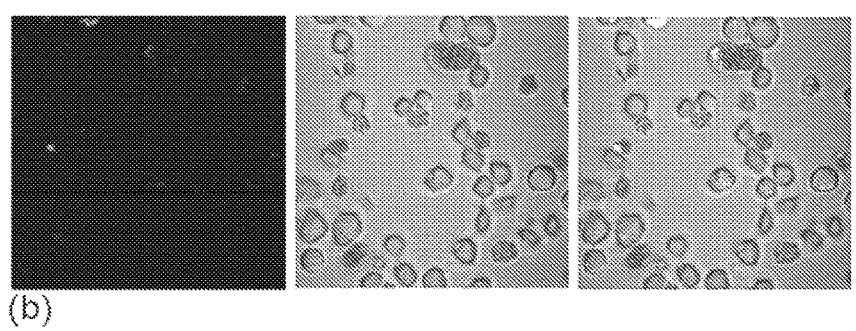

FIG. 15. Expression and anchoring of noda capsid aplha protein (magnification ×60). (a) Confirmation of the anchoring of alpha protein on the plasma membrane of Sf9-II infected with Bac-noda. (b) No anchoring of alpha protein observed on the plasma membrane of Sf9-II cells infected with wild type baculovirus. The cells were cultured on the sterile cover slips and infected at an MOI of 0.1. Cells are fixed with 4% PFA and blocked with 2% bovine serum albumin for 30 min at 37° C. The alpha protein is stained with the polyclonal anti-guinea pig antibody (1:300) followed by the secondary FITC-conjugated rabbit anti-guinea pig Mab (1:100 dilution, Dako).

FIG. 15(a) shows that rVP1 is localized at the plasma membrane, thus demonstrating the anchoring of rVP1 on the surface of the Sf-9 cells.

Figure 16:
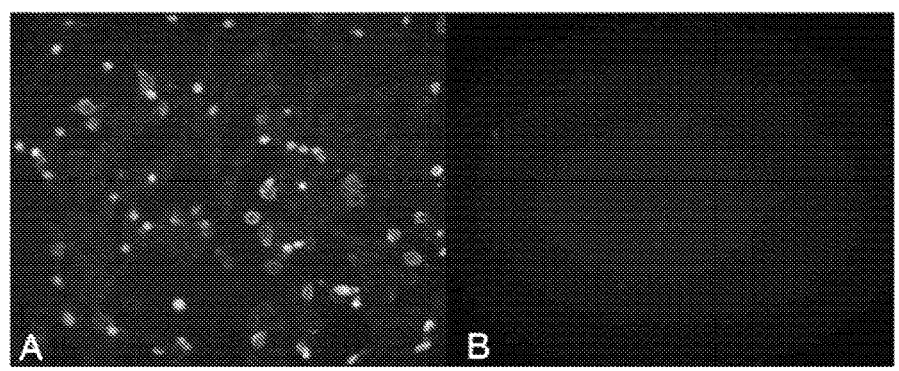

FIG. 16. Transduction and expression of VP1 in Vero cells (magnification ×40). Vero cells were incubated with multiplicity of infection (MOI) of 200 and stained with anti-VP1 monoclonal antibody followed by FITC-conjugated secondary antibody at 48 h post infection (A) Live Bac-VP1-transduced Vero cells (B) Vero cells incubated with inactivated Bac-VP1.

Light grey portions of FIG. 16 indicate where VP1 is expressed. Hence, FIG. 16 shows that VP1 is well expressed in Vero cells transduced with live Bac-VP1 compared to inactivated Bac-VP1.

Figure 17:
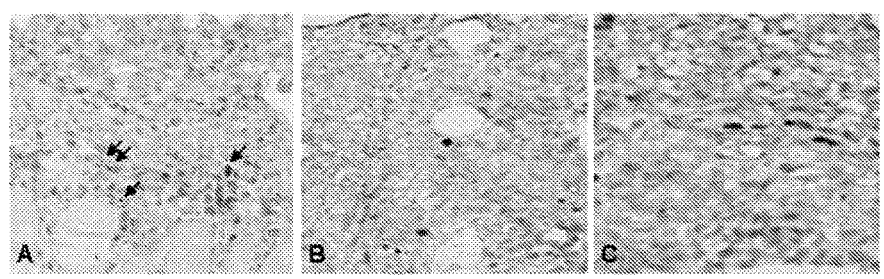

FIG. 17. Baculovirus transduction of mouse muscle tissue in vivo (magnification ×40). Six days after first immunization, muscular tissue samples were embedded in paraffin and sectioned. Immunohistochemical staining was carried out using anti-VP1 monoclonal antibody and HRP-conjugated rabbit anti-mouse antibody. (A) Bac-VP1, (B) WT-Bac (C) PBS injected mice are shown. Arrows indicate where VPlis expressed. FIG. 17 therefore shows that VP1 is expressed in mouse muscle tissue from mice transduced with Bac-VP1 whereas there is no expression of VP1 in the negative controls.

Figure 18:
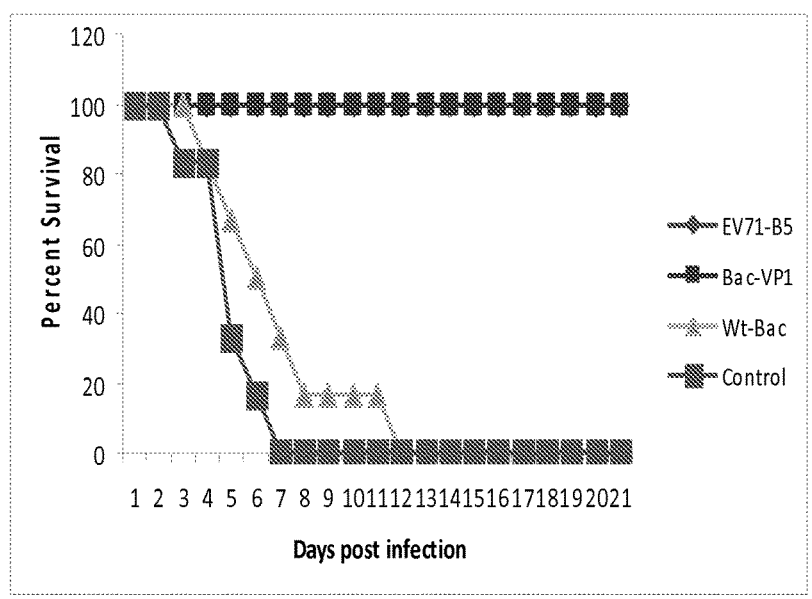

FIG. 18. Protection of mice from lethal EV71 virus challenge. Groups of mice (n=6) were vaccinated two times on 14 days interval. Wild-type baculovirus and PBS immunized mice served as negative control. Mice were monitored for survival throughout a 21-day observation period. The results were expressed in terms of percent survival. As can be seen from the results, EV71-B5 and Bac-VP1 (results are overlapping on FIG. 18) immunized mice showed a 100% survival after 7 days compared to none of the control mice.

Figure 19:
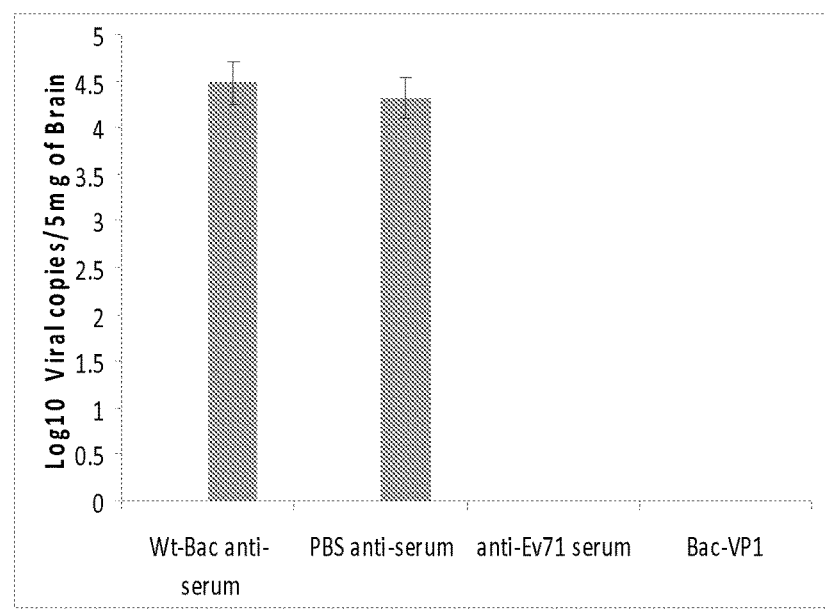

FIG. 19. Real-time RT-PCR quantification of EV71 copy numbers. RNA was extracted from the brain tissue and samples for the control were collected at 7 dpi, and samples for the prophylactically treated mice collected at 20 dpi. A 112-bp segment of the EV715' UTR region served as the target of qRT-PCR primers. The plasmid encoding the full-length genome of EV71 was employed to obtain the standard curve for quantifying the viral copy numbers. The data represent the means±SD of three independent assays.

As can be seen from FIG. 19, there were significant amounts of viral RNA from the brain tissue of mice inoculated with wild-type Baculovirus anti-serum and PBS anti-serum compared to mice inoculated with anti-EV71 serum and Bac-VP1 anti-serum. This therefore demonstrates the efficacy of anti-serum from Bac-VP1 inoculated organisms for providing passive protection against VP1.

FIG. 20. Schematic diagram of various expression cassettes. (A) Expression cassette with ie1 promoter and gp64 signal peptide; (B) Expression cassette with ie1 promoter, gp64 promoter and transmembrane region; (C) Expression cassette with ie1 promoter, gp64 promoter, transmembrane region and gp64 cytoplasmic region.

TABLES

Table 1. Primer sequences for constructing the recombinant BAC-VP1 fusion genes.

Table 2. Primer sequences for constructing the recombinant BAC-PCV2 capsid fusion gene for ORF2 of PCV2.

Table 3. Primer sequences for constructing the recombinant BAC-PRRSV nucleocapsid protein (ORF7) fusion genes.

Table 4. Examples of antigenic peptides.

Sequences

SEQ ID NO: 1: Forward primer for amplifying the entire full length of VP1 gene with additional overlapping region of gp64 signal sequence.

SEQ ID NO: 2: Reverse primer for amplifying the entire full length of VP1 gene with additional overlapping region of H3N2-HA transmembrane sequence.

SEQ ID NO: 3: Reverse primer for amplifying the C-terminus VP1 with entire sequence of H3N2-HA transmembrane sequence.

SEQ ID NO: 4: Forward primer for amplifying the entire overlapping region of gp64 signal sequence at N-terminus.

SEQ ID NO: 5: Reverse primer for amplifying the entire overlapping region of gp64 cytoplasmic domain (CTD) at C-terminus.

SEQ ID NO: 6: Forward primer for amplifying the ie1 promoter.

SEQ ID NO: 7: Reverse primer for amplifying the ie1 promoter.

SEQ ID NO: 8: Forward, primer for amplifying the capsid 76 F region of PCV2.

SEQ ID NO: 9: Reverse primer for amplifying the capsid 135 R region of PCV2.

SEQ ID NO: 10: Forward primer for amplifying the capsid 121 F region of PCV2.

SEQ ID NO: 11: Reverse primer for amplifying the capsid 180 R region of PCV2.

SEQ ID NO: 12: Forward primer for amplifying the capsid ORF 7 F region of PRRSV.

SEQ ID NO: 13: Reverse primer for amplifying the capsid ORF 7 R region of PRRSV.

SEQ ID NO: 14: Sequence of N-terminal gp64 signal peptide (20 amino acids).

SEQ ID NO: 15: Full length sequence of gp64 cytoplasmic domain (CTD), containing 7 amino acids.

SEQ ID NO:16 Truncated sequence of gp64 cytoplasmic domain containing 6 amino acids (CTD)

SEQ ID NO:17: Sequence of the H3N2-HA transmembrane domain.

SEQ ID NO:18: Sequence of the White Spot Syndrome Virus ie1 promoter.

SEQ ID NO:19: Sequence of VP1 of EV71 virus.

SEQ ID NO:20: Sequence of PCV2 PRF2 capsid protein.

SEQ ID NO:21: Sequence of ORF7 of PRRSV capsid protein.

SEQ ID NO:22: Sequence of fish nodavirus capsid protein alpha.

SEQ ID NO:23 EV71-VP1-167th-178th amino acids

SEQ ID NO:24 EV71-VP1-209th-222nd amino acids

SEQ ID NO:25 EV71-VP1-240th-260th amino acids

SEQ ID NO:26 PCV2-ORF2-100th to 150th amino acids

SEQ ID NO:27 PCV2-ORF2-151st to 200th amino acids

SEQ ID NO:28 PRRSV-ORF7-18th to 57th amino acids

SEQ ID NO:29 PRRSV-ORF7-58th to 123rd amino acids

SEQ ID NO:30 PRRSV-ORF5-28th to 65th amino acids

SEQ ID NO:31 PRRSV-ORF5-132nd to 200th amino acids

SEQ ID NO:32 PRRSV-ORF 5-a combination of 28th to 65th and 132 to 200th amino acids SEQ ID NO:33 Amino Acid Sequence of VP1 of EV71 virus corresponding to nucleic acid sequence SEQ ID NO:19 EV71-VP1

SEQ ID NO:34 Amino Acid Sequence of PCV2 capsid protein corresponding to nucleic acid sequence SEQ ID NO. 20 Sequence of PCV2 capsid protein-PCV2 PRF2

SEQ ID NO:35 Amino Acid Sequence of ORF7 of PRRSV capsid protein corresponding to nucleic acid sequence SEQ ID NO: 21 Sequence of ORF7 of PRRSV capsid protein-PRRSV ORF7

SEQ ID NO:36 Amino Acid Sequence of fish nodavirus capsid protein corresponding to nucleic acid sequence SEQ ID NO:22: Sequence of fish nodavirus capsid protein-Capsid protein Alpha SEQ ID NO: 37 Forward primer for amplifying nodavirus capsid region SEQ ID NO: 38 Reverse primer for amplifying nodavirus capsid region SEQ ID NO: 39 Alternative reverse primer for amplifying nodavirus capsid region SEQ ID NO: 40 Forward primer for detecting VP1 mRNA SEQ ID NO: 41 Reverse primer for detecting VP1 mRNA Definitions As used herein, the term "comprising" means "including principally, but not necessarily solely". Furthermore, variations of the word "comprising", such as "comprise" and "comprises", have correspondingly varied meanings.

As used herein the terms "treating" and "treatment" refer to any and all uses which remedy a condition or symptoms, prevent the establishment of a condition or disease, or otherwise prevent, hinder, retard, ameliorate or reverse the progression of a condition or disease or other undesirable symptoms in any way whatsoever.

As used herein the term "effective amount" includes within its meaning a non-toxic but sufficient amount of an agent or compound to provide the desired effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein, the terms "polypeptide", "peptide" and "protein" are used interchangeably to refer to a polymer of amino acid residues and to fragments, variants, analogues, orthologues or homologues thereof. Thus, these terms apply both to amino acid polymers in which one or more amino acid residues is a synthetic non-naturally occurring amino acid, such as a chemical analogue of a corresponding naturally occurring amino acid, as well as to naturally-occurring amino acid polymers.

As used herein, the terms "polynucleotide" or "nucleic acid" are used interchangeably and designate a molecule comprising one or more nucleotides, or an oligonucleotide, or a fragment thereof, including but not limited to RNA or DNA nucleotides or combinations thereof.

Within the scope of the terms "protein", "polypeptide", "peptide", "polynucleotide" and "nucleic acid" as used herein are fragments and variants thereof, including but not limited to reverse compliment and antisense forms of polynucleotides and nucleic acids.

The term "fragment" refers to a polynucleotide or polypeptide sequence that encodes a constituent or is a constituent of a full-length protein or gene. In terms of the polypeptide, the fragment may possess qualitative biological activity in common with the full-length protein, for example, a fragment may contain or encode one or more epitopes, such as immunodominant epitopes, that allow similar immune response to be raised to the fragment, or sequence encoded by the fragment, as to the full length sequence, or sequence encoded by the fragment.

The term "variant" as used herein refers to substantially similar sequences. Generally, nucleic acid sequence variants may encode polypeptides which possess qualitative biological activity in common. Generally, polypeptide sequence variants may also possess qualitative biological activity in common. Further, these polypeptide sequence variants may share at least 50%, 55%, 60%, 65%, 70%, 75%, 80%, 85%, 90%, 95%, 96%, 97%, 98% or 99% sequence identity.

As used herein, the term "expression vector" means a nucleic acid that has the ability confer expression of a nucleic acid fragment to which it is operably linked, in a cell or cell-free expression system. Within the context of the present invention, it is to be understood that an expression vector that comprises a promoter as defined herein may be a plasmid, bacteriophage, phagemid, cosmid, virus subgenomic or genomic fragment, or other nucleic acid capable of maintaining and or replicating heterologous DNA in an expressible format should it be introduced into a cell.

As used herein, the term "expression system" refers to a combination of an expression vector and the host for the vector that provide a context to allow foreign gene expression in a host cell, that is, enabling the production of proteins at detectable levels. Examples of expression systems include, but are not limited to viral expression systems, bacterial-based systems, such as *Escherichia coli*, yeast systems, such as *Saccharomyces cerevisiae, Pichia pastoris*, insect cell based systems, such as the baculovirus system, mammalian systems such as the Vero system, other eukaryotic systems, such as the *Leishamani* expression system.

As used herein, the term "host cell" refers to a cell used to produce the protein encoded within the expression cassette of the present invention. Examples of such host cells include an eukaryotic cell or more specific a mammalian cell; insect cell; fish cell; yeast cell; or plant cell. Examples of such cells include, but are not limited to human TK-143b cells, monkey Marc 145 cells, Vero cells and porcine PK15 cells, *Spodoptera frugiperda* Sf9 and Sf-21 cells. Hink's *Trichoplusia ni* Tn-368 and BTI-TN-5B1-4 cells, carp epithelioma papillosum cells (EPC), CHSE-214, fathead minnow (FHM), brown bullhead (BB), bluegill fry (BF2), or white sturgeon skin (WSSK-1). As used herein, the term "cassette" refers to the part of the expression vector which encodes sequences of interest for expression by the vector. For example, the cassette may refer to the part of the expression vector which encodes an N-terminal gp64 signal peptide and an antigenic peptide. The cassette may further comprise sequences encoding other components, for example a C-terminal hemagglutinin (e.g. H3N2-HA transmembrane domain) transmembrane domain and a gp64 cytoplasmic domain.

As used herein, the term "operably linked" refers to transcriptional and translational regulatory polynucleotides that are positioned relative to a polypeptide-encoding polynucleotide in a manner such that the polynucleotide is transcribed and the polypeptide is translated.

As used herein, the term "promoter" includes transcriptional regulatory sequences of a genomic gene, including the TATA box or initiator element, which may be required for accurate transcription initiation, with or without additional regulatory elements which alter gene expression in response to developmental and/or external stimuli, or in a tissue-specific manner. In the present context, the term "promoter" is also used to describe a recombinant, synthetic or fusion molecule, or derivative or fragment, for example a truncated sequence of the promoter, which confers, activates or enhances the expression of a nucleic acid molecule to which it is operably linked, and which encodes a peptide.

The cis-elements in the ie1 promoter are shown in FIG. 13. As shown in FIG. 13, truncation analysis can be performed to identify the minimal promoter region using luciferase gene reporter assay. The minimal region of ie1 promoter was identified by progressively deleting the promoter from the 5' end. In one embodiment, for the ie1 promoter for White Spot Syndrome Virus (WSSV), minimal promoter activity was observed between positions −189 and +1 of the gene.

As used herein, the phrase "disease associated with a virus" means any disease, disease state or disorder caused by or associated with a virus.

As used herein, the term "antigen" refers to a substance which is capable of being recognized by the immune system of an organism. An immunogen is an antigen capable of stimulating an immune response when administered to an organism. Both terms are interchangeably used herein. As used herein, an "antigenic peptide" is a peptide or polypeptide sequence capable of being expressed in the present expression system.

As used herein, the term "modulating" when used in relation to an immune response means increasing or decreasing, either directly or indirectly, an immune response against an antigen.

As used herein, the term "signal peptide" refers to an amino acid sequence which is capable of initiating the passage of a polypeptide, to which it is operably linked, into the endoplasmic reticulum (ER) of a host cell. The signal peptide is generally cleaved off by an endopeptidase (e.g. a specific ER-located signal peptidase) to release the (mature) polypeptide although there are instances in which a signal peptide may not be cleaved. The length of a signal peptide is typically in the range from about 10 to about 40 amino acids. In one embodiment as used herein, the term "a nucleic acid sequence encoding a signal peptide" does not include within its scope a nucleic acid sequence encoding the full length sequence of the homologous polypeptide for which a signal peptide naturally initiates passage into the endoplasmic reticulum. Examples of possible signal peptides include the luciferase signal peptide and honeybee mellittin signal peptide. For example, in one embodiment, the signal peptide of gp64 may be used. In a particular embodiment, the signal peptide of gp64 is the protein encoded by SEQ ID NO: 14 or a variant thereof.

A nucleic acid sequence as described herein can include additional nucleotides as required, for example to facilitate expression. For example, a linker sequence may be provided between the signal peptide and the antigenic peptide and/or between the antigenic peptide and the transmembrane domain, if present, as required. The nucleic acid sequence can further or alternatively comprise linker sequences as required between any other sequences contained in the expression cassette. Such linker sequences may be heterologous or homologous. The linker sequence can be between 1 and 40 amino acids, between 10 and 25 amino acids, between 6 to 10 amino acids or for example, 2, 3, 4 or 5 amino acids.

As used herein, the term "vaccine" refers to a suspension of whole (live or inactivated), or fractionated bacteria/viruses rendered nonpathogenic or less pathogenic. Vaccines can be classified broadly in three general groups: attenuated viruses, inactivated (killed) virions, and purified viral components (subunit vaccines). The vaccines obtained on the basis of the expression cassette of the present invention belong to the group of subunit vaccines.

As used herein, the term "adjuvant" refers to an agent that may stimulate the immune system and increase the response to an antigen or immunogen.

As used herein, the term "vaccination vector" refers to an expression vector which when introduced into a suitable host cell, will result in the expression of antigenic peptides which can be tailored to stimulate a range of immune responses, including antibody, T helper cell (CD4+ T cell), and cytotoxic T lymphocyte (CTL, CD8+ T cell) mediated immunity.

As used herein, the term "immunogenic composition" refers to a composition which when administered to a human or animal, results in an immune response, including antibody, T helper cell (CD4+ T cell), and cytotoxic T lymphocyte (CTL, CD8+ T cell) mediated immunity.

As used herein, the term "cytoplasmic domain" (or "CTD") refers to an amino acid sequence which provides an anchoring domain that allows the fusion protein to be expressed on the surface of the envelope of a recombinant virus, such as baculovirus. The cytoplasmic domain can be between 5 and 40 amino acids, between 10 and 25 amino acids, between 6 to 10 amino acids or for example, 2, 3, 4 or 5 amino acids.

As used herein, the term "gp64 cytoplasmic domain" is a region of 7 amino acids as shown in SEQ ID NO:15. In one embodiment, the gp64 cytoplasmic domain is a variant of the gp64 CTD as shown in SEQ ID NO: 16. Other examples of variants of gp64 cytoplasmic domain can comprise a gp64 cytoplasmic domain having a 80% or 85% or 90%, or 92%, or 95% or 96% or 98% or 99% sequence identity to SEQ ID NO: 15.

As used herein, the term "transmembrane domain" refers to an amino acid sequence which spans within the membrane of a cell. The transmembrane domain can be from about 5 to about 60 amino acids, from about 5 to about 40 amino acids, from about 10 to about 25 amino acids, from about 6 to about 10 amino acids or for example, the sequence may comprise or consist of 2, 3, 4, 5, 6, 7, 8, 9, 10, 11, 12, 13, 14, 15, 16, 17; 18, 19, 20, 21, 22, 23, 24 or 25 amino acids. The transmembrane domain may be the gp64 transmembrane domain or may be any other transmembrane domain that is suitable for use in this system, for example, the transmembrane domain may be a glycoprotein transmembrane domain, such as a hemagglutinin transmembrane domain, which is a glycoprotein on the influenza surface that allows the virus to bind to cellular sialic acid and fuse with the host membrane. Examples of hemagglutinine transmembrane domains, include but are not limited to H1, H2, H3, H4, H5, H6, H7, H8, H9, H10, H11, H12, H13, H14, H15 and H16.

In one embodiment, the hemagglutinin transmembrane domain is a H3N2 transmembrane domain or a H5N1 transmembrane domain. The H3N2 transmembrane domain for example contains cysteine residues can undergo pamitoylation and thereby get attached to the SF9-II plasma membrane and enable the localization of VP1 protein on the surface. As used herein, the term "gp64 transmembrane domain" is a region of 27 amino acids as shown in SEQ ID NO:17. In one embodiment, the gp64 cytoplasmic domain is a truncated sequence of the gp64 transmembrane domain and comprises or consists of from about 10 to about 25 amino acids, from about 6 to about 10 amino acids or 2, 3, 4, 5, 6, 7, 8, 9, 10, 11, 12, 13, 14, 15, 16, 17, 18, 19, 20, 21, 22, 23, 24 or 25 amino acids as shown in SEQ ID NO: 17.

As used herein the term "functional fragment" refers to a fragment of a protein domain which is able to perform the full function of the protein domain.

In the present invention different expression systems can be used to express the expression cassette described herein. Examples of such expression systems include, but are not limited to viral expression systems, such as adenovirus, lentivirus, adeno-associated virus, retrovirus and baculovirus expression systems, bacterial-based systems, such as *Escherichia coli*, yeast systems, such as *Saccharomyces cerevisiae, Pichia pastoris*, insect cell based systems, such as the InsectSelect Stable Expression System, mammalian systems such as the Vero system, and other eukaryotic systems, such as the *Leishamani* expression system, In one example, a baculovirus expression system is used.

Baculoviruses were originally thought to only infect insects and invertebrates and have been widely used for the production of numerous recombinant proteins in insect cells. However, the development of the *Autographa californica* multiple nuclear polyhedrosis virus (AcMNPV) into a eukaryotic protein expression system during the early 1980s marked the start of the wide utilization of this virus for expressing heterologous proteins in insect cells. Since then, numerous attempts have been made to develop baculovirus vectors that can carry mammalian expression cassettes for in vitro and in vivo gene therapy studies, drug screening, and recombinant protein expression. The major advantages of the baculovirus expression system include its large insertion capacity, its relatively easy construction, as well as the presence of strong promoters and post-translational processing abilities.

The expression of foreign proteins on the baculovirus membrane (surface display), using the gp64 full length protein, was first developed in the mid 1990s. Typically, an "expression vector", comprising a gene encoding a heterologous protein or peptide of interest is fused in-frame at the N-terminus of a full-length gp64 gene under the control of polyhedrin or p10 promoter. Such constructs are then integrated into the baculovirus genome using various suitable methods, such as the Bac-To-Bac system (Invitrogen). The fusion protein, after expression as an additional copy, is translocated to the plasma membrane and incorporated into viral envelope, resulting in expression of the heterologous protein on the baculovirus membrane surface.

In one embodiment, the invention relates to an expression cassette that comprises an ie1 promoter or truncated sequence thereof, a N-terminal gp64 signal peptide and an antigenic peptide, wherein the promoter is operably linked to the nucleic acid sequence (see FIG. 20A). In one embodiment, the aforementioned gp64 signal peptide is encoded by SEQ ID NO:14 or a variant thereof.

In another embodiment, the invention relates to a novel "expression cassette" that comprises an ie1 promoter or a variant thereof, a N-terminal signal peptide, such as a N-terminal gp64 signal peptide, an antigenic peptide, and a transmembrane region, wherein the promoter is operably linked to the nucleic acid sequence (see FIG. 20B). In one embodiment, the aforementioned transmembrane region is a H3N2, or H5N1 or H3N2-HA (SEQ ID NO: 17 or a variant thereof) transmembrane region.

In another embodiment, the invention relates to an expression cassette that comprises an ie1 promoter or truncated sequence thereof, a N-terminal signal peptide, such as a N-terminal gp64 signal peptide, an antigenic peptide, a transmembrane region, and a gp64 cytoplasmic region, wherein the promoter is operably linked to the nucleic acid sequence (see FIG. 20C). In one embodiment, the aforementioned cytoplasmic region is encoded by SEQ ID NO: 15 or 16 or variants thereof.

In one embodiment, the invention relates to an expression cassette that encodes at least the N-terminal gp64 signal peptide (20 amino acids [aa]), an antigenic capsid protein, C-terminal H3N2-HA-transmembrane domain (27 aa) and a gp64-cytoplasmic domain (6 aa) and which is transcriptionally controlled by the WSSV immediate early ie1 promoter (SEQ ID NO: 18) or a fragment or truncated version thereof.

In some embodiments, the promoter sequence is the region of the WSSV ie1 promoter. In one embodiment, the promoter sequence is the region of the WSSV ie1 promoter comprising or consisting of the sequence of nucleotides from positions −189 to +1 of the gene. The "expression cassette" can be incorporated into an "expression vector" suitable for use in a viral expression system, such as a baculoviruses and subsequently incorporated into the baculoviral genome using various means commonly known to those of skill in the art.

In particular, the inventors have demonstrated the application of a viral expression system, such as a baculovirus expression system, as an immunizing reagent against virus through synergistic surface display and gene transduction of antigenic peptides, for example viral proteins, for example viral capsid protein. The efficient display of immunodominant protein on the surface of recombinant virus, such as a baculovirus, confers a major advantage in vaccination strategies. In addition to application of this viral expression system as a vaccination vector for EV71, PCV2, PRRSV, nodavirus, as described herein, the viral membrane display system can also be used to characterize the structure and function of a wide variety of antigenic peptides, for example viral proteins, for example viral capsid proteins.

For example, under the control of the ie1 promoter from white spot syndrome virus, the VP1 viral capsid gene was efficiently expressed in both insect and mammalian cells using a viral vector, such as a baculovirus vector. Antibodies raised in mice by using the baculovirus-surface displayed VP1 as an immunogen efficiently neutralized the infectivity of EV71 in vitro. Hence, this recombinant baculovirus is a good vaccine for the treatment, for example, of EV71 infections.

In an exemplary embodiment, the expression cassette of the invention was cloned using standard molecular techniques known in the art into an expression vector suitable for use in a chosen protein expression system, such as the Bac-to-Bac baculovirus expression system (Invitrogen).

Multiple copies of the expression vector were then obtained by transfecting the expression vector into a cell line, such as *E. coli*. Next the expression vector was transfected into a host cell line such as insect Sf9 and the budded virus particles released into the medium in which the host cell line was growing were harvested at 4 days post transfection. The virus particles were then used as a subunit vaccine for inoculation of mice.

The same strategy utilizing the design of the "expression cassette" was also applied to generate genetically engineered viruses to express immunogenic peptides or proteins of Porcine Circovirus 2 (PCV2) and Porcine respiratory and reproductive syndrome virus (PRRSV). The expression cassettes were inserted in the viral genome, such as the Baculovirus genome and were found to be abundantly expressed and displayed on the surface of the respective virus. In one example described herein, the genetically recombinant Baculovirus displayed immunogenic peptides from PCV2 or PRRSV and were used to immunize guinea pigs producing (neutralizing) antibodies which efficiently neutralized the infectivity of the respective viruses.

The herein mentioned generation of recombinant Baculovirus expressing the immunogenic peptides from PCV2 or PRRSV and its utility as an immunogen against the infection of the respective viruses shows the broad utility of the design of the "expression cassette" and demonstrates its potential as a tool for generating vaccines against antigenic peptides, for example viral proteins, for example capsid proteins of any virus and also for producing antigens for use in a diagnostic kit.

Methods, Kits and Systems for Presenting or Displaying Biomolecules

The present invention discloses biomolecule surface display systems, with particular application of such systems to display of peptides as vaccines. As will be apparent to persons of skill in the art, these biomolecule surface display systems are not limited to the particular applications disclosed herein, but find broad application in any situation in which it is desirable to present a biomolecule, and in particular, an antigenic peptide, for example a viral protein, for example a viral capsid protein.

Accordingly, in one embodiment, the present invention discloses methods, kits and systems for vaccine production involving surface display of peptides. These methods, kits and systems may for example utilize the baculovirus-based surface display systems exemplified herein in relation to production of a vaccine against viruses. However, persons of skill in the art will recognize and understand that the methods, kits and systems for vaccine production involving surface display of peptides are not limited to production of the vaccines disclosed herein.

Accordingly, the present invention provides methods for presenting or displaying a polypeptide, wherein said methods comprise:
(a) inserting a nucleic acid encoding said polypeptide into an expression vector as disclosed herein;
(b) transfecting at least one host cell with said expression vector; and
(c) expressing said polypeptide from said expression vector wherein said polypeptide is presented or displayed on the surface membrane of a baculovirus.

The present invention further provides systems for presenting or displaying a polypeptide, wherein said systems comprise:
(a) a nucleic acid encoding said polypeptide inserted into an expression vector, wherein said expression vector comprises an ie1 promoter from white spot syndrome virus;
(b) means for transfecting at least one host cell with said expression vector; and
(c) means for expressing said polypeptide from said expression vector
wherein said polypeptide is presented or displayed on the surface membrane of a virus such as baculovirus.

Antigenic Peptides

Antigenic peptides as used in the present invention includes polypeptide or peptide capable of being expressed in the present expression system. The antigenic peptide as used herein may be a bacterial, viral or protozoan antigen, including but not limited to viral envelope, viral capsid, viral immunodominant regions or viral surface antigen. In one embodiment, the antigen is a viral capsid peptide antigen. Using the system herein described it is possible to express both viral envelope and non-envelope proteins. The antigenic peptides as used herein may or may not include within its scope a nucleic acid sequence encoding the full length sequence of the polypeptide. The antigenic peptide used herein may be a fragment that may contain or encode one or more epitopes, such as immunodominant epitopes, that allow similar immune response to be raised to the fragment, or sequence encoded by the fragment, as to the full length sequence or sequence encoded by the fragment. The antigenic fragment can be between 1 to 500 amino acids, between 20-400 amino acids, between 30-300 amino acids, for example, the fragment may be about 100, 200, 250, 300 or 350 amino acids.

The antigenic peptide may be a viral, bacterial or protozoan peptide, for example a viral capsid peptide, selected from the group of bacteria from the genus of *Borrelia, Trypanosoma cruzi, Chlamydia trachomatis*, Cytomegalovirus, Dengue, Epstein-Barr Virus, EV71, Hepatitis A, Hepatitis B, Hepatitis C, Hepatitis D, Hepatitis E, Herpes, HIV, Human T-lymphotropic virus (HTLV), Influenza virus, for example H5N1, H1N1, *Plasmodium falciparum, Plasmodium vivax, Plasmodium ovale, Plasmodium malariae*, Measles virus, nodavirus, betanodavirus, PCV2, PRRSV, Rubella virus, SARS coronavirus, Toxoplasma, *Treponema pallidum*, West Nile virus or Varicella virus. The peptide may be expressed by or derived from the virus, bacteria or protozoa. The peptide may be recombinant or purified.

The antigenic peptide as used herein may be a capsid protein of a virus or a retrovirus or an immunogenic fragment thereof.

The antigenic peptide as used herein may be obtained from an EV71 virus, for example the antigenic peptide is selected from the group consisting of VP0, VP1 and VP3 or an epitope or fragment thereof, for example the antigenic peptide may comprise or consist of amino acids 167-178 of VP1 (SEQ ID NO:23); amino acids 209-222 of VP1 (SEQ ID NO:24); and/or amino acids 240-260 of VP1 (SEQ ID NO:25) or an immunogenic fragment thereof. An exemplary embodiment of an antigenic peptide is illustrated in FIG. 3.

The antigenic peptide as used herein may be obtained from a PCV2 virus, for example the antigenic peptide is PCV2 capsid protein encoded by ORF2, or an epitope or fragment thereof, for example the antigenic peptide may comprise or consist of amino acids 100-150 of ORF2 (SEQ ID NO:26) and/or amino acids 151-200 of ORF2 (SEQ ID NO:27) or an immunogenic fragment thereof.

The antigenic peptide as used herein may be obtained from a PRRSV virus, for example the antigenic peptide is encoded by an ORF selected from the group consisting of ORF-4, ORF-5 (major envelope protein) and ORF-7 (nucleocapsid protein) or an epitope or fragment thereof, for example the antigenic peptide may comprise or consist of amino acids 18-57 of ORF7 (SEQ ID NO:28); amino acids 58-123 of ORF7 (SEQ ID NO:29); amino acids 28-65 of ORF5 (SEQ ID NO:30) and/or amino acids 132-200 of ORF7 (SEQ ID NO:31) or an immunogenic fragment thereof.

The antigenic peptide as used herein may be obtained from bacteria from the genus of Borrelia, for example the antigenic peptide is selected from the group consisting of p41 and C6 or an epitope or fragment thereof.

The antigenic peptide as used herein may be obtained from Trypanosoma cruzi, for example the antigenic peptide is TcF or an epitope or fragment thereof.

The antigenic peptide as used herein may be obtained from Chlamydia bacteria, for example the antigenic peptide is major outer membrane protein or an epitope or fragment thereof.

The antigenic peptide as used herein may be obtained from a Dengue virus, for example the antigenic peptide is non-structural protein 1 or an epitope or fragment thereof.

The antigenic peptide as used herein may be obtained from an Epstein-Barr Virus, for example the antigenic peptide is non-structural protein 1 or an epitope or fragment thereof.

The antigenic peptide as used herein may be obtained from a Hepatitis A, Hepatitis B, Hepatitis C, Hepatitis D, Hepatitis E, and the antigenic peptide is for example HBsAg or E1 peptide, or an epitope or fragment thereof.

The antigenic peptide as used herein may be obtained from a Herpes virus, for example the antigenic peptide is H1 or an epitope or fragment thereof.

The antigenic peptide as used herein may be obtained from an HIV virus, for example the antigenic peptide is gp120 or an epitope or fragment thereof.

The antigenic peptide as used herein may be obtained from a Human T-lymphotropic virus (HTLV), for example the antigenic peptide is gp46 or an epitope or fragment thereof.

The antigenic peptide as used herein may be obtained from an Influenza virus, such as H5N1 or H1N1, and the antigenic peptide is for example hemagglutinin or an epitope or fragment thereof.

The antigenic peptide as used herein may be obtained from Plasmodium falciparum, Plasmodium vivax, Plasmodium ovale, Plasmodium malariae, and the antigenic peptide is for example the antigenic peptide is merozoite surface protein 2 (MSP2) or an epitope or fragment thereof.

The antigenic peptide as used herein may be obtained from a measles virus, for example the antigenic peptide is measles or an epitope or fragment thereof.

The antigenic peptide as used herein may be obtained from a rubella virus, for example the antigenic peptide is E1 or an epitope or fragment thereof.

The antigenic peptide as used herein may be obtained from a SARS coronavirus, and the antigenic peptide is for example S protein or an epitope or fragment thereof.

The antigenic peptide as used herein may be obtained from Toxoplasma, and the antigenic peptide is for example SAG-1 or P30 or an epitope or fragment thereof.

The antigenic peptide as used herein may be obtained from Treponema pallidum, and the antigenic peptide is for example major outer sheath protein (Msp) or an epitope or fragment thereof.

The antigenic peptide as used herein may be obtained from West Nile Virus, and the antigenic peptide is for example E protein or an epitope or fragment thereof.

The antigenic peptide as used herein may be obtained from nodavirus, for example the antigenic peptide is the capsid protein of nodavirus or an epitope or fragment thereof.

Examples of antigenic peptides that may be used in the present invention are shown in Table 4, below:

TABLE 4

| SEQ ID NO | Fragment |
|---|---|
| 23 | EV71-VP1-167$^{th}$-178$^{th}$ amino acids RESLAWQTATNP |
| 24 | EV71-VP1-209$^{th}$-222$^{nd}$ amino acids YPTFGEHKQEKDLE |
| 25 | EV71-VP1-240$^{th}$-260$^{th}$ amino acids GSSKSKYPLVVRIYMRMKHVR |
| 26 | PCV2-ORF2-100$^{th}$ to 150$^{th}$ amino acids KVKVEFWPCSPITQGDRGVGSSAVILDDNFVTKATALTY DPYVNYSSRHTI |
| 27 | PCV2-ORF2-151$^{st}$ to 200$^{th}$ amino acids TQPFSYHSRYFTPKPVLDSTIDYFQPNNKRNQLWLRLQT AGNVDHVGLGT |
| 28 | PRRSV-ORF7-18$^{th}$ to 57$^{th}$ amino acids PVNQLCQMLGKIIAQQNQSRGKGPGKKNKKKNPEKPHFP L |
| 29 | PRRSV-ORF7-58$^{th}$ to 123$^{rd}$ amino acids ATEDDVRHHFTPSERQLCLSSIQTAFNQGAGTCTLSDSG RISYTVEFSLPTHHTVRLIRVTASPSA |
| 30 | PRRSV-ORF5-28$^{th}$ to 65$^{th}$ amino acids LANASNSSSSHLQLIYNLTLCELNGTDWLANRFDWAVE |
| 31 | PRRSV-ORF5-132$^{nd}$ to 200$^{th}$ amino acids MSWRYACTRYTNFLLDTKGRLYRWRSPVIIEKRGKVEVE GHLIDLKRVVLDGSVATPITRVSAEQWGRP |
| 32 | PRRSV-ORF 5-a combination of 28$^{th}$ to 65$^{th}$ and 132$^{nd}$ to 200$^{th}$ amino acids LANASNSSSSHLQLIYNLTLCELNGTDWLANRFDWAVE MSWRYACTRYTNFLLDTKGRLYRWRSPVIIEKRGKVEVE GHLIDLKRVVLDGSVATPITRVSAEQWGRP |

The present invention also includes an antibody which is specific for the antigenic peptide expressed in the host cell.

Immunogenic Compositions or Vaccines

The present invention also provides immunogenic compositions or vaccines as described herein for the treatment or prevention of a disease in a subject, wherein said disease is associated with an infection, for example a viral infection, such as EV71, PCV2, PRRSV or nodavirus, and wherein said vaccine comprises an expression vector comprising a nucleic acid encoding an antigenic peptide, for example a viral capsid protein, such that in use said antigenic peptide is expressed by said expression vector in said subject.

The subject may be mammalian, avian, crustacean, a jawless fish, a bony fish, reptilian or amphibian. The subject may be human, non-human primate, avian, fish, shrimp, crab, lobster or porcine.

The expression vector may comprise a promoter. In one embodiment, the promoter comprises or consist of an ie1 promoter from white spot syndrome virus as described herein. The promoter may be operably linked to the nucleic acid encoding an antigenic peptide.

The present invention also provides immunogenic compositions or vaccines as described herein comprising the expression vectors, host cells or compositions as herein described, for the treatment or prevention of a disease in a subject, wherein said disease is associated with a pathogen, for example a bacterium, virus or protozoan, such as enterovirus 71 (EV71), Porcine Circovirus 2 (PCV2), Porcine Respiratory and Reproductive Syndrome Virus (PRRSV), fish nodavirus or influenza A (HA, H3N2).

The present invention also provides immunogenic compositions or vaccines comprising the expression vectors, host cells or compositions as herein described, for the treatment or prevention of a disease in a subject, wherein said disease is selected from the group of hand foot and mouth disease, postweaning multisystemic wasting syndrome, porcine reproductive and respiratory Syndrome, herpes, influenza, cancer, hepatitis, toxoplasmosis, syphilis, malaria or viral nervous necrosis, borreliosis, chagas disease, *chlamydia*, dengue fever, encephalitis, hepatitis A, hepatitis B, hepatitis C, hepatitis D, hepatitis E, herpes, HIV, HTLV, influenza, for example H5N1, H1N1, malaria, measles, nodaviral associated disease, PCV2-associated disease, porcine reproductive and respiratory syndrome virus (PRRSV), rubella, SARS, toxoplasmosis, syphilis, west nile fever, or varicella (chicken pox).

Expression Vectors and Host Cells

The present invention also provides expression vectors comprising a nucleic acid encoding an antigenic peptide, for example wherein said antigenic peptide comprises a viral capsid peptide.

The present invention further provides expression vectors comprising a nucleic acid encoding an antigenic peptide, for use in the treatment or prevention of a disease in a subject, wherein said disease is associated with a viral infection, such that in use said antigenic peptide is expressed by said expression vector in said subject. Examples of expression vectors suitable for use in baculovirus include but is not limited to BAC-TO-BAC™ (Invitrogen), BACULODIRECT™ (Invitrogen), BACPAK6/BACULOGOLD™ (BD Bio sciences/Clonetech), FLASHBAC™ (Genway) and PROEASY™ (AB Vector technologies).

The present invention also provides host cells comprising the expression vectors as described herein. In one embodiment, the host cells are insect cells, for example the host cells may be SF9 cells such as SF9-II, SF9-III. In another embodiment the host cells are mammalian cells, for example human, monkey or porcine cells, such as human TK-143b cells, monkey Marc145 cells or Vero cells, or porcine PK15 cells. In another embodiment the host cells are piscine cells, for example carp epithelioma papillosum cells (EPC).

Compositions and Immunopotentiating Agents

The present invention further contemplates compositions comprising an immunopotentiating agent, diluent, adjuvant or excipient.

The immunopotentiating agents may be formulated into a composition as neutral or salt forms. Pharmaceutically acceptable salts include the acid addition salts (formed with free amino groups of the peptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic basis such as, for example, sodium, potassium, ammonium, calcium, or ferric hydroxides, and such organic basis as isopropylamine, trimethylamine, 2-ethylamino ethanol, histidine, procaine, and the like.

In general, suitable compositions may be prepared according to methods which are known to those of ordinary skill in the art and may include pharmaceutically acceptable diluents, adjuvants and/or excipients. The diluents, adjuvants and excipients must be "acceptable" in terms of being compatible with the other ingredients of the composition, and not deleterious to the recipient thereof.

Examples of pharmaceutically acceptable diluents are demineralised or distilled water; saline solution; vegetable based oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 1% to 99.9% by weight of the compositions. Most preferably, the diluent is saline.

For administration as an injectable solution or suspension, non-toxic parenterally acceptable diluents or carriers can include, Ringer's solution, medium chain triglyceride (MCT), isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants can be divided into several major groups including mineral containing adjuvant compositions, oil-emulsion adjuvants, saponin adjuvant formulations, virosomes and virus like particles (VLPs), bacterial or microbial derivatives and immunostimulatory oligonucleotides. Common examples of adjuvants include but not limited to Adjuvant 65 (containing peanut oil, mannide monooleate and aluminum monostearate); a Montanide adjuvant such as Montanide Incomplete Seppic Adjuvant (USA), for example Montanide ISA 50, 51 or 720, Freund's complete or incomplete adjuvant; mineral gels such as aluminum hydroxide, aluminum phosphate and alum; surfactants such as hexadecylamine, octadecylamine, lysolecithin, dimethyldioctadecyl-ammonium bromide, N,N-dioctadecyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; QS-21, Detox-PC, MPL such as 3D-MPL, MoGM-CSF, TiterMax-G, CRL-1005, GERBU, TERamide, PSC97B, Adjumer, PG-026, GSK-1, GcMAF, B-alethine, MPC-026, Adjuvax CpG ODN, Betafectin, Alum, MF59 and oil emulsions, such as water-in-oil or oil-in-water emulsions.

Solid forms for oral administration may contain binders acceptable in human and veterinary pharmaceutical practice, sweeteners, disintegrating agents, diluents, flavourings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

Emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

One or more agents as disclosed herein or above can be included in the preparation of compositions of the present invention. Such preparation uses routine methods known to persons skilled in the art. Typically, such compositions are prepared as injectables, either as liquid solutions or suspensions; solid forms suitable for solution in, or suspension in, liquid prior to injection may also be prepared. The preparation may also be emulsified. The active immunogenic ingredients are often mixed with excipients that are pharmaceutically acceptable and compatible with the active ingredient.

Routes of Administration

According to the methods of present invention, vaccines and compositions may be administered by any suitable route, either systemically, regionally or locally. The particular route of administration to be used in any given circumstance will depend on a number of factors, including the nature of the disease to be treated, the severity and extent of the disease, the required dosage of the particular compounds to be delivered and the potential side-effects of the desired vaccines or compositions.

For example, in circumstances where it is required that appropriate concentrations of the desired vaccines or compositions are delivered directly to the site to be treated, administration may be regional rather than systemic. Regional administration provides the capability of delivering very high local concentrations of the desired vaccines or compositions to the required site and thus is suitable for achieving the desired therapeutic or preventative effect whilst avoiding exposure of other organs of the body to the vaccines or compositions and thereby potentially reducing side effects.

By way of example, administration according to embodiments of the invention may be achieved by any standard routes, including intracavitary, intravesical, intramuscular, intraarterial, intravenous, subcutaneous, topical or oral. Intracavitary administration may be intraperitoneal or intrapleural.

If desired, devices or compositions containing expression cassettes as described herein, suitable for sustained or intermittent release could be, in effect, implanted in the body or topically applied thereto for the relatively slow release of such materials into the body.

Administration of an expression vector or host cell may include delivery via direct oral intake, systemic injection, or delivery to selected tissue(s) or cells, or indirectly via delivery to cells isolated from a subject or a compatible donor.

With regard to nucleic acid based compositions, all modes of delivery of such compositions are contemplated by the present invention. Delivery of these compositions to cells or tissues of an animal may be facilitated by microprojectile bombardment, liposome mediated transfection (e.g., lipofectin or lipofectamine), electroporation, calcium phosphate or DEAE-dextran-mediated transfection, for example. In an alternate embodiment, a synthetic construct may be used as a therapeutic or prophylactic composition in the form of a "naked DNA" composition as is known in the art. A discussion of suitable delivery methods may be found in Chapter 9 of CURRENT PROTOCOLS IN MOLECULAR BIOLOGY (Eds. Ausubel et al.; John Wiley & Sons Inc., 1997 Edition) or on the Internet site DNAvaccine.com. The compositions may be administered by intradermal (e.g., using Panjet™ delivery) or intramuscular routes.

The step of introducing the synthetic polynucleotide into a target cell will differ depending on the intended use and species, and can involve one or more of non-viral and viral vectors, cationic liposomes, retroviruses, and baculoviruses such as, for example, described in Mulligan, R. C., (1993 Science 260 926-932) which is hereby incorporated by reference. Such methods can include, for example:

A. Local application of the synthetic polynucleotide by injection (Wolff et al., 1990, Science 247 1465-1468, which is hereby incorporated by reference), surgical implantation, instillation or any other means. This method can also be used in combination with local application by injection, surgical implantation, instillation or any other means, of cells responsive to the protein encoded by the synthetic polynucleotide so as to increase the effectiveness of that treatment. This method can also be used in combination with local application by injection, surgical implantation, instillation or any other means, of another factor or factors required for the activity of said protein.

B. General systemic delivery by injection of DNA, (Calabretta et al., 1993, Cancer Treat. Rev. 19 169-179, which is incorporated herein by reference), or RNA, alone or in combination with liposomes (Zhu et al., 1993, Science 261 209-212, which is incorporated herein by reference), viral capsids or nanoparticles (Bertling et al., 1991, Biotech. Appl. Biochem. 13 390-405, which is incorporated herein by reference) or any other mediator of delivery. Improved targeting might be achieved by linking the synthetic polynucleotide to a targeting molecule (the so-called "magic bullet" approach employing, for example, an antibody), or by local application by injection, surgical implantation or any other means, of another factor or factors required for the activity of the protein encoding said synthetic polynucleotide, or of cells responsive to said protein.

C. Injection or implantation or delivery by any means, of cells that have been modified ex vivo by transfection (for example, in the presence of calcium phosphate: Chen et al., 1987, Mole. Cell Biochem. 7 2745-2752, or of cationic lipids and polyamines: Rose et al., 1991, BioTech. 10 520-525, which articles are incorporated herein by reference), infection, injection, electroporation (Shigekawa et al., 1988, BioTech. 6 742-751, which is incorporated herein by reference) or any other way so as to increase the expression of said synthetic polynucleotide in those cells. The modification can be mediated by plasmid, bacteriophage, cosmid, viral (such as adenoviral or retroviral; Mulligan, 1993, Science 260 926-932; Miller, 1992, Nature 357 455-460; Salmons et al., 1993, Hum. Gen. Ther. 4 129-141, which articles are incorporated herein by reference) or other vectors, or other agents of modification such as liposomes (Zhu et al., 1993, Science 261 209-212, which is incorporated herein by reference), viral capsids or nanoparticles (Bertling et al., 1991, Biotech. Appl. Biochem. 13 390-405, which is incorporated herein by reference), or any other mediator of modification. The use of cells as a delivery vehicle for genes or gene products has been described by Barr et al., 1991, Science 254 1507-1512 and by Dhawan et al., 1991, Science 254 1509-1512, which articles are incorporated herein by reference. Treated cells can be delivered in combination with any nutrient, growth factor, matrix or other agent that will promote their survival in the treated subject.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

Dosages

The effective dose level of the administered compound for any particular subject will depend upon a variety of factors including: the type of disease being treated and the stage of the disease; the activity of the compound employed; the composition employed; the age, body weight, general health, sex and diet of the subject; the time of administration; the route of administration; the rate of sequestration of compounds; the duration of the treatment; drugs used in combination or coincidental with the treatment, together with other related factors well known in the art.

One skilled in the art would be able, by routine experimentation, to determine an effective, non-toxic dosage which would be required to treat applicable conditions. These will most often be determined on a case-by-case basis.

In terms of weight, a therapeutically effective dosage of a composition for administration to a patient is expected to be in the range of about 0.01 mg to about 150 mg per kg body weight per 24 hours; typically, about 0.1 mg to about 150 mg per kg body weight per 24 hours; about 0.1 mg to about 100 mg per kg body weight per 24 hours; about 0.5 mg to about 100 mg per kg body weight per 24 hours; or about 1.0 mg to about 100 mg per kg body weight per 24 hours. More typically, an effective dose range is expected to be in the range of about 5 mg to about 50 mg per kg body weight per 24 hours.

Alternatively, an effective dosage may be up to about 5000 mg/m$^2$. Generally, an effective dosage is expected to be in the range of about 10 to about 5000 mg/m$^2$, typically about 10 to about 2500 mg/m$^2$, about 25 to about 2000 mg/m$^2$, about 50 to about 1500 mg/m$^2$, about 50 to about 1000 mg/m$^2$, or about 75 to about 600 mg/m$^2$.

Further, it will be apparent to one of ordinary skill in the art that the optimal quantity and spacing of individual dosages will be determined by the nature and extent of the condition being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per unit time, can be ascertained by those skilled in the art using conventional course of treatment determination tests.

Assessment of Immunisation Efficacy

The effectiveness of an immunisation undertaken in accordance with the methods of the present invention may be assessed using any suitable technique. For example, CTL lysis assays may be employed using stimulated splenocytes or peripheral blood mononuclear cells (PBMC) on peptide coated or recombinant virus infected cells using $^{51}$Cr labelled target cells. Such assays can be performed using, for example, primate, porcine, guinea pigs, mouse or human cells (Allen et al., 2000, J. Immunol. 164(9): 4968-4978 also Woodberry et al., infra). Alternatively, the efficacy of the immunisation may be monitored using one or more techniques including, but not limited to, HLA class I Tetramer staining of both fresh and stimulated PBMCs (see for example Allen et al., supra), proliferation assays (Allen et al., supra), ELISPOT™ Assays; direct or indirect immunofluorescence assay and intracellular IFN-gamma staining (Allen et al., supra), ELISA Assays for linear B cell responses, and Western blots of cell samples expressing the antigenic peptides as described herein. Immunogold electron microscopic techniques could alternatively or additionally be used.

Kits

The present invention provides kits for use in treating or preventing a disease in a subject, wherein said disease is associated with a virus, and wherein said kit comprises the vaccines, expression vectors, host cells or compositions as described herein.

In the context of the present invention, a compartmentalised kit includes any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion.

Typically, a kit of the present invention will also include instructions for using the kit components to conduct the appropriate methods.

The present invention will now be described by reference to the following examples, which should not be construed in any way as limiting the scope of the invention.

EXAMPLES

Example 1—Construction of the Recombinant Bac-VP1

The full-length open reading frame (ORF) of the VP1 gene of EV71 virus (C4strain) was amplified and cloned in to pFASTBacHT A plasmid (Invitrogen, SanDiego, Calif.). To efficiently display VP1 on the baculovirus envelope, an additional signal sequence of gp64 was genetically fused to the N-terminus of VP1, while the C-terminus was flanked by H3N2-HA transmembrane domain and CTD of gp64 for the recognition with nucleocapsid and subsequent protein incorporation into budding virions. In total five primers (listed in the Table 1) were designed to construct the fusion genes.

Figure 1:
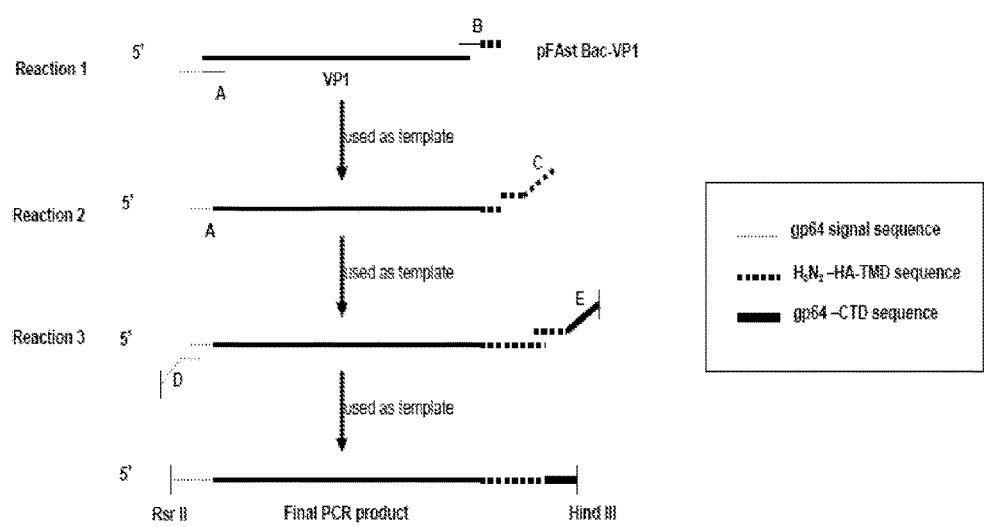
FIG. 1. Construction of fusion genes using PCR as described in detail in Example 1. Three sequential PCR reactions were performed to generate the final PCR product which contains the gp64 signal sequence, H3N2-HA transmembrane domain and cytoplasmic domain (CTD) of gp64.
Figure 2:
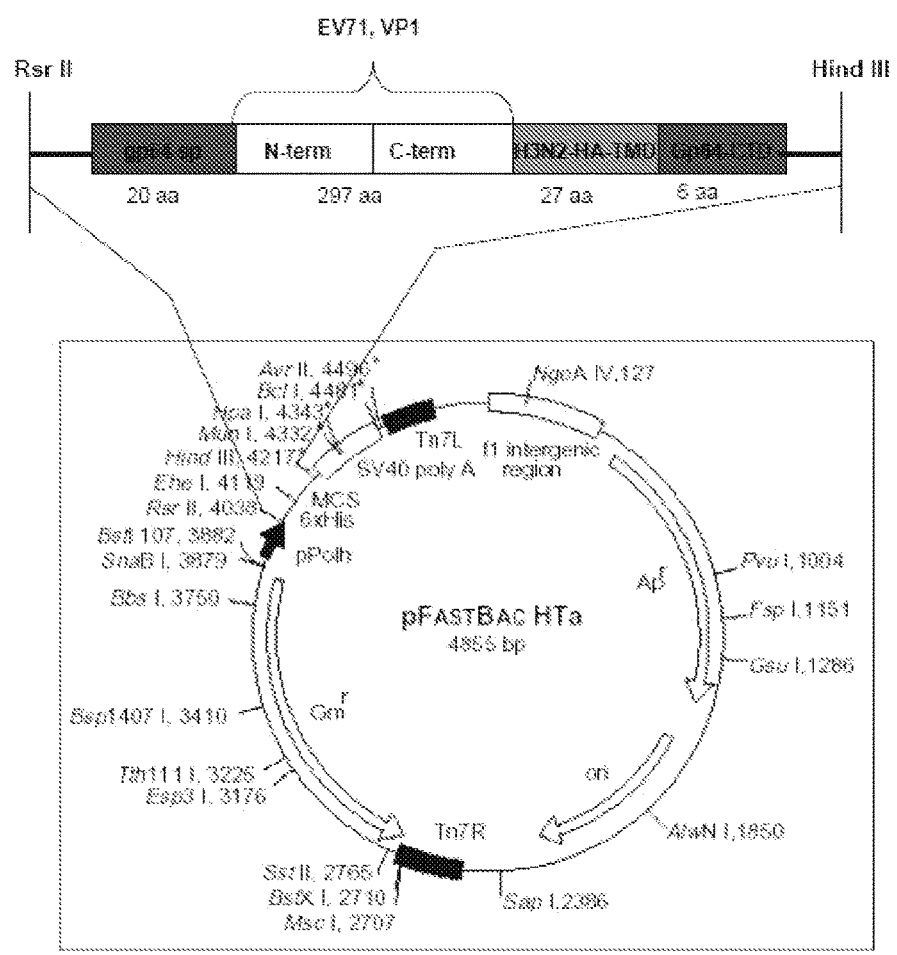
FIG. 2. Illustration of recombinant baculovirus vector manufactured according to Example 1. Using the EV71 genome as a template, primers listed in table 1 were used to amplify the VP1 gene, which was then inserted into the pBac-HTA vector. The resultant plasmids were named as pBac-VP1.

FIG. 1 illustrates the entire process for generating the fusion genes. Primers A (SEQ ID NO:1) and B (SEQ ID NO:2) were used to amplify the entire full length VP1 gene along with additional overlapping region of gp64 signal sequence, H3N2-HA transmembrane region at N-terminus and C-terminus of VP1 respectively. Using the above purified reaction mixture as template, Primers A (SEQ ID NO: 1) and C (SEQ ID NO: 3) were used to overlap the C-terminus of VP1 with the entire sequence of H3N2-HA transmembrane domain. Finally, using the above purified reaction mixture as a template, Primers D (SEQ ID NO: 4) and E (SEQ ID NO: 5) were used to overlap the entire region of gp64 signal sequence, gp64 CTD region at N-terminus and C-terminus respectively. The resultant PCR products were purified and cloned into pFASTBacHT, a plasmid with appropriate restriction sites. Primer D (SEQ ID NO:4) and Primer E (SEQ ID NO:5) were designed to add restriction enzymes sites RsrII and Hind III at both termini. The ie1 promoter was amplified from WSSV DNA using Primer F (SEQ ID NO: 6) and Primer G (SEQ ID NO: 7) and then inserted into pFASTBac HT A using AccI and Rsr II restriction sites. FIG. 2 shows the fully constructed recombinant baculoviral vector.

TABLE 1

| Primer | Orientation | Primer sequence |
|--------|-------------|-----------------|
| A | Forward | TTTGGCGGCGGCGGCGCATTCTGCCTTTGCGGGAGATAGGGTGGCAGATGTAATTG |
| B | Reverse | CATGATATGGCAAAGGAAATCCATAGGATCCAAAGAGTGGTGATCGCTGTGCGAC |
| C | Reverse | TTGGCAGGCCCACATGATGAACCCCAACAAAGCAACACAAAGCAAAAAACATGATATGGCAAAGGAAATCCA |
| D | Forward | AATCGGTCCGATGGTAAGCGCTATTGTTTTATATGTGCTTTTGGCGGCGGCGGCGCATTCTG |
| E | Reverse | AATAAGCTTTTAATATTGTCTATTACGGTTTTGGCAGGCCCACATGATGAACC |
| F | Forward | CCTACGTATCAATTTTATGTGGCTAATGGAGA |
| G | Reverse | CGCGTCGACCTTGAGTGGAGAGAGAGCTAGTTATAA |

In Table 1, note that the following SEQ ID NO: identifiers apply:
Primer A: SEQ ID NO:1
Primer B: SEQ ID NO:2
Primer C: SEQ ID NO:3
Primer D: SEQ ID NO:4
Primer E: SEQ ID NO:5
Primer F: SEQ ID NO:6
Primer G: SEQ ID NO:7

Generation of Recombinant Baculovirus

For the generation of recombinant baculoviruses, the constructs were integrated into the baculovirus genome within DH10Bac (Invitrogen) through site specific transposition using Bac-To-Bac system (Invitrogen). The recombinant bacmids were then transfected into Sf9 cells, and the budded virus particles released into the medium were harvested at 4 days post transfection. The subsequent viral amplification and plaque purification were performed in insect Sf9-II cell lines supplemented with Sf9-II serum free medium. $TCID_{50}$ were determined by endpoint dilution method. Ideally, during virus replication the gp64 signal sequence directs the translocation of the chimeric protein in to insect cell plasma membrane and is cleaved after protein anchoring thus exposing VP1 N-terminus to the outer surface. H3N2-HA transmembrane domain enables the protein to anchor on the plasma membrane, while the gp64 CTD mediates (1) the recognition of budding baculovirus nucleocapsid with the membrane-bound protein and (2) the incorporation of the anchored protein in to the viral envelope.

Confirmation of Recombinant Protein (rVP1) Expression in Sf9-II Cells

Figure 4:
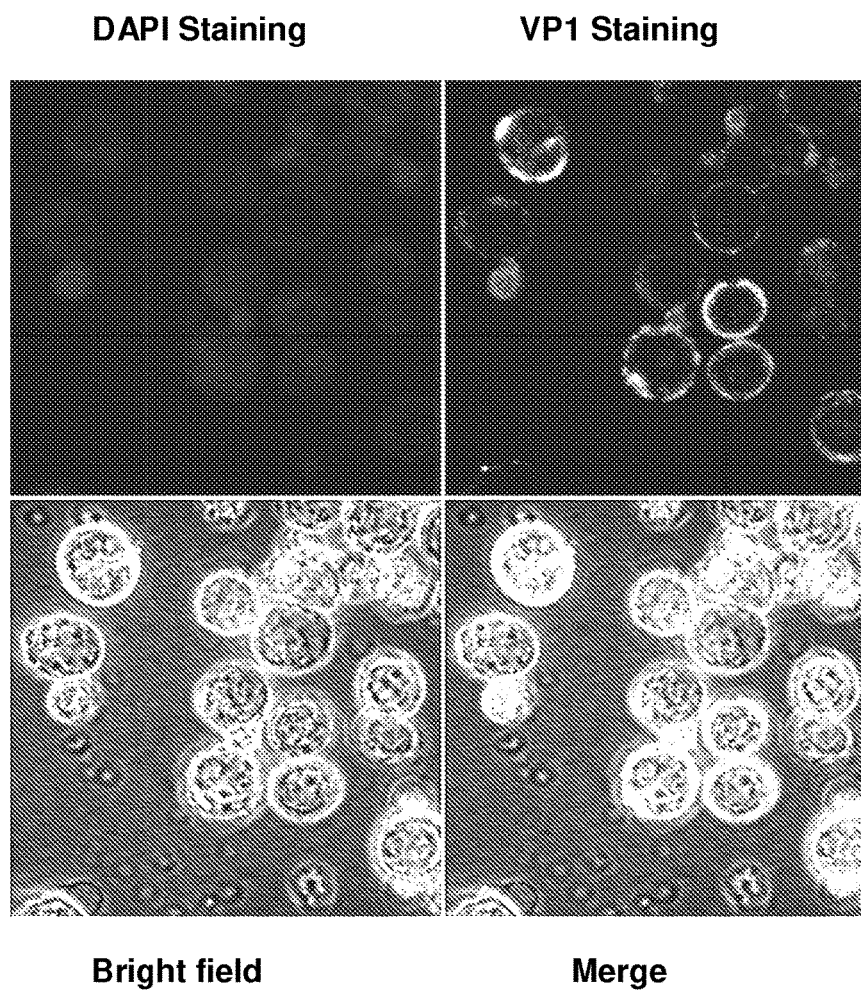
FIG. 4. Anchoring of rVP1 of EV71 (magnification ×60). To determine whether rVP1 protein was properly translocated to the cell surface, the cells were cultured on sterile coverslips, infected at a multiplicity of infection (MOI) of 10, and subjected to immunofluorescence staining with confocal microscopy 2 days post-infection. The DAPI staining was used to detect the cell nuclei whilst green fluorescently labeled anti-VP1 polyclonal antibodies were used to detect the rVP1 displayed by Bac-VP1 recombinant baculoviruses.

To confirm the expression of rVP1 in insect Sf9-II cells, the cells were infected, used as control, and infected as mentioned above. The pattern of the rVP1 display on the SF9-II cells surface was shown in FIG. 3. To confirm whether the rVP1 were properly translocated on the surface on the plasma membrane, the cells were cultured on sterile cover slips, infected by rBac-VP1[1], wild type baculovirus (WT-Bac) and subjected to immunofluorescence labelling/confocal microscopy visualization at 2 dpi (FIG. 4). Two days after infection, the supernatant was removed, and the cells were fixed by 4% PFA for 1 h at 4° C., rinsed with 1 ml of PBS and then blocked with 2% BSA in PBS (1 ml) for 30 min at 37° C. The cells were then incubated with the primary antibody (anti-VP1, polyclonal anti-guinea pig (1:500) for 1 h at 37° C., followed by PBS washes 3 times. The cells were then incubated with the secondary antibody (FITC-conjugated goat anti-guinea pig antibody, 1:100) for 1 h at 37° C. followed by 3 PBS washes. Protein localization was visualized by a confocal microscope (Leica). The merged photographs illustrate the co-localization of rVP1 with plasma membrane. rBac-VP1[1] expressed proteins that were detected by polyclonal anti-VP1 guinea pig (1:500) antibody. Based on the co-localization of the rVP1 with the plasma membrane, it was confirmed that rVP1 were translocated and anchored on the plasma membrane.

Display of rVP1 on the Baculoviral Envelope

To examine whether the rVP1 anchored on the plasma membrane was successfully displayed on the baculoviral envelope, rBac-VP1[1] rBac-VP1[2] and WTBac were purified by sucrose gradient centrifugation and subject to western blot using polyclonal anti-VP1 (guinea pig) antibody as primary antibody followed by anti-guinea pig HRP labelled as secondary antibody (FIG. 5). The obtained rVP1 as shown in FIG. 5, the recombinant viruses were produced by infecting cells at MOI 0.1 and harvested at 4 days post infection. The virus supernatant was individually purified by sucrose gradient ultracentrifugation (O'Reilly, 1992). In total 200 ml virus was pelleted by ultracentrifugation at 90,000×g (Beckman coulter) for 2 hr, and the pellets were pooled and resuspended in 2 ml PBS. For further virus purification, the concentrated virus (1 ml) were loaded onto a sucrose gradient (10 ml) consisting of 20, 35, 50 and 60% (wt/wt) sucrose solution. After centrifugation at 90,000×g for 2.5 hrs, baculovirus that sediment near 50% sucrose was collected by syringe diluted in 8 PBS and ultracentrifuged at 90,000×g for 2 h. The purified virus pellet resuspended in 0.5 ml PBS and then was subject to immunogold electron microscopy as follows. The carbon-coated copper grid was floated on top of drop of blocking solution (PBS containing 1% BSA and 25 mM glycine pH 6.2) for 30 min and washed with PBS 3×5 min. Following the washing, the grid was transferred on to drop (25 µl each) of the anti-mouse VP1 pAb solution (1:500) and incubated for 30 min at room temperature. After three washes with PBS, the grid was then floated on the goat anti-mouse Ab conjugated with 5-nm gold particle (1:25) for 30 min at room temperature. After washing with PBS, the grid was negatively stained with 2% phosphotungstic acid (PTA, Sigma) for 2 min and air-dried at room temperature. The grids were then examined under transmission electron microscope. FIG. 6 reveals no gold particles on the surface of WT-Bac, whereas gold particles were observed on the surface of rBac-VP1[1], indicating the incorporation and display of rVP1 on the viral envelope.

The incorporation of rVP1 in to the purified Baculoviruses (rBac-VP1[1], rBACVP1[2]) is visualized by SDS-PAGE/Western blot and quantitated by Infrared scanning densitometry (FIG. 7) by which the amount of rVP1 incorporated in to the viruses were quantified based on the comparison between the intensity of purified protein Vs incorporated rVP1. As compared, the expression level of rVP1 on the baculoviral envelope rBac-VP1[1] is ~2 times higher than the wild type EV71 virus (B5 strain) and ~14 times higher than the rBac-VP1[2]. As shown in FIG. 5, the purified viruses were subject to SDS-PAGE and western blot using anti-VP1 mAb as primary antibody and secondary Donkey anti-mouse IRdye800 (1:5000). Protein quantitation was done using the Odyssey v1.1 IR imaging system (LI-COR).

Immunogen Eliciting Properties of VP1-Recombinant Baculoviruses (Bac-VP1)

To examine whether the VP1 displayed on baculovirus could serve as immunogen eliciting anti-VP1 antibodies in vivo, 2 groups of mice, each comprising 8 female BALB/c mice (6 weeks old, purchased NUS Animal care) were immunized subcutaneously with $1.2 \times 10^7$ PFU purified Bac-VP1, respectively. As negative control, five mice were injected with purified wild type baculovirus WT or PBS. As a positive control, chemically inactivated EV71 (B5) virus ($10^7$) was injected. Each mouse was injected with the purified virus (200 µl) along with 200 µl complete Freund's adjuvant. Two weeks after the primary injection the mice received one booster shot 9 using equal amount of the purified virus with the incomplete Freund's adjuvant. Blood samples were taken from the tail vein on week 6 and heat inactivated.

The EV71 strain was grown in RD cells. The individual viruses (100 $TCID_{50}$ units) were incubated at 37° C. for 1 h in serially diluted test or control sera (heat inactivated at 56° C. for 30 min). After 3 days, EV71 infected monolayers were fixed with 95% ethanol and 5% acetone at −20° C. for 20 min and anti-EV71 (guinea pig) antibody as the first antibody and a FITC-conjugated goat anti-guinea pig IgG as the second antibody. Cells were observed using a fluorescence microscope and the ability of the test sera to neutralize virus infectivity was determined. The reciprocal of the highest dilution of the test serum at which the fluorescence was 50% or less than that of the virus infected control well was taken as the virus neutralization titer. As shown in the FIG. 8, the negative control wild type baculovirus and PBS induced no neutralization while rBac-VP1[1] induced neutralization titer up to $2^{7.2}$, whereas the inactivated EV71 induced neutralization titer up to $2^{4.9}$.

These data indicated that the incorporated rVP1 successfully induced functional antibodies. Although baculovirus displaying immunogen as a vaccine candidate has been proposed, this is the first report that demonstrates the recombinant baculovirus with abundant expression of the immunogen (capsid protein VP1) on its surface. Baculovirus encoding the expression cassette which comprises gp64 (full length) as a fusion partners did not efficiently display the immunogen on its surface, which is confirmed by VP1 quantitation assay and virus neutralization assay. However the possibility of immune response against the exposed fusion gp64 counterpart could hinder the vaccine efficiency.

In the present example, the signal peptide sequence contains only the signal sequence from the gp64 gene (SEQ ID NO:14), whereas the full length gp64 gene contains gp64 signal sequence, ectodomain, transmembrane domain (TMD) and cytoplasmic domain (CTD). When expressing VP1 in the present novel expression cassette with gp64 signal sequence, H3N2-HA transmembrane domain and gp64 CTD, the final expressed protein will be more or less similar to the native VP1 molecular weight, while in case of the normal expression cassette, VP1 is inserted in between the gp64 signal sequence and the mature gp64 domain (includes gp64 ectodomain, transmembrane domain, cytoplasmic domains) so the final total expressed protein will be higher than the normal size of the VP1 protein (see FIG. 5)

Thus, in this invention the generated recombinant baculovirus (rBac-VP1[1]) encoding the novel "expression cassette" which comprises gp64 signal peptide (20 aa), H3N2-HA transmembrane domain (27 aa) and gp64 cytoplasmic domain (6 aa) as fusion partner, displays more rVP1 on Baculoviral envelope and confers higher immune response against VP1 as compared with rBac-VP1[2] and inactivated EV71 (B5) virus. As EV71 infection became one of the major infectious diseases which infects infants and children worldwide, especially in Asian countries, the development of EV71 vaccine has become imminent. The approval of this novel vaccine can open a new avenue to EV71 vaccine development and also provide alternative approach to the existing vaccine technology.

This example therefore clearly demonstrates the use of the expression cassette of the invention, which does not require the full length gp64 sequence, for the expression of a target antigen (VP1 in this particular example) on the surface of baculovirus as well as the subsequent use of the baculovirus to successfully elicit an immune response, thereby functioning as a vaccine against a target pathogen.

Example 2—Use of Expression Cassette for Displaying Other Immunogenic Proteins/Peptides on the Surface of the Baculovirus In accordance with the present invention, the applicability of the "expression cassette" for displaying other immunogenic proteins/peptides on the surface of the Baculovirus and its utility as an immunogen was ascertained by expressing immunogenic peptides/proteins from Porcine Circovirus 2 (PCV2), Porcine Respiratory and Reproductive Syndrome Virus (PRRSV) and Betanodavirus. The PCV2 and PRRSV are major pathogens infecting swine and they inflict heavy economic losses in the swine production industry. The PCV2 is a non enveloped virus with a single structural protein and the PRRSV is an enveloped virus with multiple structural components. The Betanodavirus belongs to the members of the Nodaviridae family, are the causative agents of viral nervous necrosis in fish and infection by which cause high mortality in larvae and juveniles in a wide range of marine fish species in Asia, Europe, Australia, Martinique, and Tahit. The recombinant Baculoviruses expressing the PCV2, PRRSV and Betanodavirus immunogenic peptides/proteins from the "expression cassette", driven by the ie1 promoter, showed abundant expression and surface display on the Baculoviral envelope. The recombinant Baculovirus expressing PCV2, PRRSV and Betanodavirus immunogenic regions on their surface can be used as a vaccine against these swine pathogens.

Construction of PCV2 and PRRSV Immunogenic Regions into the Expression Cassette.

PCV2 Capsid Protein:

The capsid protein, ORF-2, of the PCV2 is the major immunogenic protein. The capsid regions that were displayed on the Baculovirus surface using the aforementioned expression cassette were obtained from the PCV2 strain BJW (GenBank: AY847748.1). The amino acids 76 to 135, 121 to 180 and 76 to 180 were fused in frame with the components of the "expression cassette" in between the N-terminal gp64 signal sequence and C terminal H3N2-HA transmembrane domain, gp64 cytoplasmic domain. The following primers were used to amplify the capsid regions of PCV2 (Table 2).

TABLE 2

| No | Primer | Orientation | Sequence |
|---|---|---|---|
| 1 | Capsid 76 F | Forward | ATTAATGATTTTCTTCCCCCAGGAG |
| 2 | Capsid 135 R | Reverse | GGCTGTGGCCTTTGTTACAAAGTTATCATC |
| 3 | Capsid 121 F | Forward | AGTGCTSTTATTCTAGATGATAACTTTGTAAC |
| 4 | Capsid 180 R | Reverse | TCTTTTGTTGTTTGGTTGGAAGTAATCAATAGTGG |

In Table 2, note that the following SEQ ID NO: identifiers apply:
Primer Capsid 76 F: SEQ ID NO:8
Primer Capsid 135 R: SEQ ID NO:9
Primer Capsid 121 F: SEQ ID NO:10
Primer Capsid 180 R: SEQ ID NO:11

The Baculovirus genomes harbouring the above mentioned regions of the PCV2 capsid protein in the "expression cassette" were constructed as described earlier and the virus was regenerated. The expression and incorporation of the PCV2 capsid protein regions on the baculovirus surface was examined by western blotting and electron microscopy as described earlier for the rBac-VP1 construct. The observations showed that indeed the capsid protein regions were displayed on the baculovirus surface and the expression levels were abundant as observed in western blot assay (FIG. 9) and Immunofluorescence assay using conformation specific monoclonal antibody 8C2. Further the antibodies obtained from guinea pigs inoculated with the above recombinant Baculovirus were able to detect PCV2 antigens in PCV2 infected PK-15 cell monolayers by immunofluorescence assay (FIG. 10).

PRRSV Nucleocapsid Protein (ORF7):

ORF5 and ORF7 of PRRSV encode the major immunogenic proteins of PRRSV. The major envelope protein (encoded by ORF5) and the nucleocapsid protein (encoded by ORF7) were displayed on the Baculovirus surface using the aforementioned expression cassette. For PRRSV major envelope protein (ORF5), deletion of its three trans-membrane spanning amino acids encourages efficient surface display by the Baculovirus. The major envelope protein does not need co-expression of the nucleocapsid protein for it to be surface displayed on Baculovirus in this manner. ORF7 and ORF5 are different ORFs, and transcribed individually. The immunogenic regions were amplified from the PRRSV strain JK100 (GenBank: AF332732.1). The proteins of interest were fused in frame with the components of the "expression cassette" in between the N-terminal gp64 and C terminal H3N2-HA transmembrane domain. The following primers were used to amplify the capsid regions of PRRSV (Table 3).

TABLE 3

| No | Primer | Orientation | Sequence |
|---|---|---|---|
| 1 | ORF7 F | Forward | ATGCCAAATAACAACGGCAAGCAGC |
| 2 | ORR7 R | Reverse | TGCTGAGGGTGATGCTGTGACGCG |

In Table 1, note that the following SEQ ID NO: identifiers apply:
Primer ORF7 F: SEQ ID NO:12
Primer ORF7 R: SEQ ID NO:13

The Baculovirus genomes harbouring the above mentioned proteins of the PRRSV in the "expression cassette" were constructed as described earlier and the virus was regenerated. The expression and incorporation of the PRRSV proteins on the baculovirus surface was examined by western blotting and electron microscopy as described earlier for the rBac-VP1[1] construct. The observations showed that indeed the proteins were efficiently displayed on the baculovirus surface and the expression levels were abundant as observed in western blot assay (FIG. 11) and Immunofluorescence assay using conformation specific monoclonal antibody specific ORF7 (5H2). Further the antibodies obtained from guinea pigs inoculated with the above recombinant Baculovirus were able to detect PRRSV antigens in PRRSV infected MARC-145 cell monolayers by Immunofluorescence assay (FIG. 12).

Construction of Betanodavirus Capsid Protein into the Expression Cassette.

The nucleocapsid alpha protein of the betanodovirus is the major immunogenic protein. The full length noda capsid alpha protein were fused in frame with the components of the "expression cassette" in between the N-terminal gp64 signal sequence and C terminal H3N2 transmembrane domain, gp64 cytoplasmic domain. The following primers were used to amplify the capsid regions of nodavirus. NodaR1 was used to add the H3N2 domain, whereas the NodaR2 was used to add the gp64 cytoplasmic domain.

```
NodaF-5'-
                                    (SEQ ID NO: 37)
AATCGGTCCGATGGTAAGCGCTATTGTTTTATATGTGCTTTTGGCGGCG

GCGGCGCATTCTGCCTTTGCGGTACGCAAAGGTGAGAAGAAATTGG

NodaR1-5'-
                                    (SEQ ID NO: 38)
TGGCAAAGGAAATCCATAGGATCCAGTTTCCCGAGTCAACCCTGGTGCAG NodaR2-
                                    (SEQ ID NO: 39)
AAGCTTATTTTAATATTGTCTATTACGGTTTTGGCAGGCCCACATGATG

AACCCCAACAAAGCAACACAAAGCAAAAAACATGATATGGCAAAGGAAA

TCCATAGGA
```

The Baculovirus genomes harbouring the above mentioned capsid alpha protein of the betanodavirus in the "expression cassette" was constructed as described earlier and the virus was regenerated. The expression and incorporation of the capsid protein on the baculovirus surface was examined by western blotting and confocal microscopy analysis as described earlier for the rBac-VP1 construct. The observations showed that indeed the proteins were efficiently displayed on the baculovirus surface and the expression levels were abundant as observed in western blot assay (FIG. 14) and confocal assay (FIG. 15) using specific anti-guinea pig polyclonal antibody against betanodavirus.

The efficient Baculovirus surface display of capsid regions shows the broad utility of the "expression cassette" for the surface display of proteins/peptides from both enveloped and non-enveloped viruses other than EV71. Further the retention of the immunogenicity of these surface displayed regions/proteins and the ability of the antibodies, raised against the surface displayed regions/proteins in guinea pigs, to recognize native antigens in the infected cells shows their usefulness as vaccine.

This example thus clearly demonstrates the workability of the expression cassette for expressing a variety of different target antigens on the surface of baculovirus.

Example 3—Use of Expression Cassette for Expression of VP1 in Vero Cells (In Vitro Transduction Assay)

Vero cells were seeded at a concentration of $2 \times 10^5$ cells into six well plates. After the cells reached 70-80% confluence, the medium was removed and cells were washed three times with PBS (pH 7.4). The cells were then incubated in media containing recombinant baculovirus (Bac-VP1) for 6 h at 27° C. As negative control Vero cells are incubated with BEI inactivated Bac-VP1 for 6 h at 27° C. After removal of virus, fresh medium was added and cultures were incubated at 37° C. At 48 h post transduction, cells were analyzed for expression of VP1 capsid protein by the indirect immunofluorescence assay (IFA). Briefly the cells were fixed with 4% paraformaldehyde and processed for the IFA using anti-VP1 monoclonal antibody followed by three washes with PBS-Tween-20 (0.1%) followed by incubation with FITC conjugated secondary anti-mouse antibody. The unbound antibodies were washed three times with PBS-Tween-20 (0.1%) and visualized under fluorescence microscope. The images obtained are shown in FIG. 16.

This example clearly demonstrates that other alternative host cells (such as the mammalian Vero cells) rather than Sf9-II insect cells can be used with the expression cassette of the present invention.

Example 4—Use of Expression Cassette for Expression of VP1 in a Whole Organism (In Vivo Transduction Assay)

For the in vivo transduction analysis, three mice from Bac-VP1, wild type baculovirus and PBS immunized group were euthanized on day 6, and muscle tissues were collected in 10% (wt/vol) buffered formalin, embedded in paraffin, and sectioned. The sections were then deparaffinized using Histo-choice (Amersco) and rehydrated in sequentially graduated ethanol baths. Slides were blocked in 0.3% nonfat milk in PBS for 30 min, followed by incubation with anti-VP1 monoclonal antibody for 1 h at 37° C. Slides were then washed 3 times in PBS and incubated with HRP-conjugated rabbit anti-mouse (Dako Cytomation, Denmark) at a dilution of 1:50 for 30 min. After washing, the slides were incubated with hematoxylin for 2-5 min and the slides were washed thrice with sterile water and the sections were mounted using mounting medium. The slides were observed under a microscope (Olympus, UK) and the images were captured by digital imaging system (Nikon, USA) (FIG. 17).

As can be seen from FIG. 16, positive staining for anti-VP1 was only observed in the muscle tissue of the mice which were inoculated with Bac-VP1. This example therefore clearly demonstrates that whole organisms inoculated with baculoviruses containing the expression cassette of the present invention can subsequently express the target antigens of the expression cassette of the present invention.

Example 5—Anti-Sera Obtained from a Whole Organism Inoculated with Baculovirus Containing the Expression Cassette can Confer Passive Protection on Another Whole Organism (Histopathological Analysis)

For this experiment, BALB/c mice were obtained were housed and bred under specific pathogen-free conditions in individual ventilated cages. To test the efficacy of the antisera from Bac-VP1 immunized mice, 1-week-old BALB/c mice (n=6) were administered with antisera intraperitoneally (ip.) one day before lethal challenge with 5 MLD$_{50}$ of EV71 B4 strain HFM 41 (5865/SIN/00009) via the ip. route. Mice (n=6) from the positive control group were given an equal amount of antisera from formalin activated EV71 virus one day before lethal virus challenge. The same procedure followed for the antisera from the wild type baculovirus and PBS control mice group (n=6). Survival rates and clinical scores of the mice were monitored daily. Total limb paralysis was used as criterion for early euthanasia (FIG. 18).

As can be seen from FIG. 18, BALB/c mice administered with antisera obtained from Bac-VP1 immunized mice showed a significant difference in survival rate compared to the control mice administered with antisera from the wild type baculovirus and PBS control mice group.

This experiment thus clearly demonstrates that anti-sera obtained from a whole organism inoculated with baculovirus containing the expression cassette (which therefore contains antibodies against a target antigen) can confer passive protection on another whole organism.

Quantitative Reverse Transcription Polymerase Chain Reaction (qRT-PCR) Assay

As a follow up to the previous experiment, brain tissues from control group (mice treated with antisera from wild type baculovirus and PBS immunized mice) and prophylactically protected mice were homogenized for total RNA extraction by Trizol reagent (Invitrogen). Extracted RNA (1 µg) was used for qRT-PCR using Quantifast SYBR Green RT-PCR kit (Qiagen, Hilden, Germany) according to the manufacturer's protocol.

5' UTR specific primers, i.e UTR-F-5'-TCCTCCGGC-CCCTGAATG-3' (SEQ ID NO: 40) and UTR-R-5'-GGA-CACCCAAAGTAGTCGGTTC-3' (SEQ ID NO: 41) were used for amplification. The qRT-PCR thermal cycling conditions were an initial incubation at 50° C. for 12 min (reverse transcription), 95° C. for 6 min (initial PCR activation step), followed by 40 cycles each of 95° C. for 12 s (denaturation), 60° C. for 30 s (combined annealing and extension), and 77° C. for 15s. Melting curve data were collected from 50-95° C. at a ramping of 1° C./5 s, and a finally cooling at 40° C. was performed. The reaction was carried out using a Rotor-Gene-Q real time PCR cycler (Qiagen). The relative expression values were normalized to the expression value of the β-tubulin housekeeping gene. Serial ten-fold dilutions of recombinant plasmid DNA containing full-length EV71 genome were included to generate a standard curve for quantitative analysis.

FIG. 19 shows that there was high expression of EV71 mRNA in the brain tissue of the control mice compared to the prophylactically protected mice, thereby showing that there is no evidence of EV71 virus in the brain tissue of prophylactically protected mice and that the expression cassette of the present invention can be used to successfully confer passive protection against a pathogenic organism.

The efficient viral surface display of EV71 peptides, PCV2 capsid regions and PRRSV nucleocapsid protein (ORF7) shows the broad utility of an "expression cassette" comprising the ie1 promoter and the signal peptide of gp64 for the surface display of capsid proteins/peptides from both enveloped and non-enveloped viruses other than EV71. Further the retention of the immunogenicity of these surface displayed regions/proteins and the ability of the antibodies, raised against the surface displayed regions/proteins in guinea pigs, to recognize native antigens in the infected cells shows their usefulness as vaccine. Additionally, an increase in the expression level of the peptides form expression cassettes comprising the ie1 promoter and signal peptide of gp64 compared to expression cassettes comprising the full-length gp64 shows further utility of the present disclosure.

The invention claimed is:

1. A baculovirus expression cassette, wherein said expression cassette comprises:
   (a) an immediate early ie1 promoter from white spot syndrome virus;
   (b) a nucleic acid sequence encoding an N-terminal gp64 signal peptide, a nucleic acid sequence encoding a viral capsid peptide, a nucleic acid sequence encoding a transmembrane region, and a nucleic acid sequence encoding a gp64 cytoplasmic region;
   in which the promoter is operably linked to the nucleic acid sequence encoding the N-terminal gp64 signal peptide,
   and wherein the gp64 cytoplasmic domain encoded by the nucleic acid sequence encoding the gp64 cytoplasmic region consists of SEQ ID NO: 16.

2. The expression cassette according to claim 1, wherein the viral capsid peptide is from a virus, or a retrovirus, or an immunogenic fragment thereof.

3. The expression cassette according to claim 1, wherein the viral capsid peptide is a peptide from a cytomegalovirus, or dengue virus, or enterovirus (EV71), or porcine circovirus (PCV2), or porcine reproductive and respiratory syndrome virus (PRRSV), or herpes simplex virus (HSV-1), or HSV-2, or Epstein-Barr virus, or poliovirus, or hepatitis A, or hepatitis B virus, or hepatitis C virus, or hepatitis D, or hepatitis E virus, or betanodavirus, or herpes, or HIV, or human T-lymphotropic virus (HTLV), or (influenza virus, or measles virus, or nodavirus, or rubella virus, or SARS virus, or West Nile virus, or varicella virus.

4. The expression cassette according to claim 3, wherein the virus is EV71 and the viral capsid peptide is selected from the group consisting of VP0, VP1, VP3 and a fragment thereof.

5. The expression cassette according to claim 3, wherein the virus is PCV2 and the viral capsid peptide is PCV2 capsid peptide encoded by ORF-2 or a fragment thereof.

6. The expression cassette according to claim 3, wherein the virus is PRRSV and the viral capsid peptide is encoded by ORF-7 (nucleocapsid protein) or a fragment thereof.

7. The expression cassette according to claim 3, wherein the virus is nodavirus and the viral capsid peptide is the capsid peptide of nodavirus or a fragment thereof.

8. The expression cassette according to claim 3, wherein the virus is betanodavirus and the viral capsid peptide is the capsid peptide of betanodavirus or a fragment thereof.

9. The expression cassette according to claim 1, wherein the transmembrane region is a glycoprotein transmembrane region.

10. The expression cassette according to claim 9, wherein the glycoprotein transmembrane region is a hemagglutinin transmembrane region.

11. The expression cassette according to claim 10, wherein the hemagglutinin transmembrane region is selected from the group consisting of H1, H2, H3, H4, H5, H6, H7, H8, H9, H10, H11, H12, H13, H14, H15 and H16.

12. The expression cassette according to claim 11, wherein the hemagglutinin transmembrane region is selected from the group consisting of H3N2 and H5N1.

13. The expression cassette according to claim 12, wherein the H3N2 transmembrane region is SEQ ID NO: 17.

14. The expression cassette according to claim 1, wherein the N-terminal gp64 signal peptide is SEQ ID NO: 14.

15. The expression cassette according to claim 1, wherein the ie1 promoter is SEQ ID NO: 18.

16. An expression vector comprising an expression cassette according to claim 1.

17. The expression vector according to claim 16, wherein the vector is compatible with a protein expression system comprising an isolated host cell selected from the group consisting of a bacteria cell, a mammalian cell, an insect cell, a fish cell, a yeast cell and a plant cell.

18. The expression vector according to claim 17, wherein the host cell is Sf9-II.

19. The expression vector according to claim 16, wherein the expression vector is suitable for use in a viral expression system.

20. The expression vector according to claim 19, wherein the viral expression system is selected from the group consisting of adenovirus, lentivirus, adeno-associated virus, retrovirus and baculovirus.

21. The expression vector according to claim 20, wherein the viral expression system is the baculovirus expression system.

22. A kit comprising an expression cassette according to claim 1 or an expression vector of claim 16 and packaging materials therefor.

23. An isolated non-human host cell comprising an expression cassette according to claim 1 or an expression vector of claim 16.

24. An immunogenic composition comprising an expression cassette according to claim 1, or an expression vector according to claim 16, together with any one or more of a pharmaceutically acceptable carrier, adjuvant, diluent or excipient.

25. A vaccine comprising an expression cassette according to claim 1, or an expression vector according to claim 16, together with any one or more of a pharmaceutically acceptable carrier, adjuvant, diluent or excipient.

26. A method for modulating an immune response, wherein said method comprises administering to a subject an effective amount of an expression cassette according to claim 1, or an expression vector according to claim 16, or an immunogenic composition of claim 24, or a vaccine according to claim 25.

27. The method according to claim 26, wherein the subject is mammalian, or avian, or crustacean, or a jawless fish, or a bony fish, or reptilian or amphibian.

28. The method according to claim 26, wherein any one of the expression cassette according to claim 1, the expression vector according to claim 16, the immunogenic composition of claim 24, or the vaccine according to claim 25 is suitable for oral administration.

29. A method for presenting, producing or displaying an antigenic peptide, wherein the method comprises:
  (a) inserting a nucleic acid encoding the antigenic peptide into an expression vector according to claim 16;
  (b) transfecting at least one isolated host cell with the expression vector; and
  (c) expressing the antigenic peptide from the expression vector;
  wherein the antigenic peptide is presented or displayed on the surface membrane of a baculovirus.

* * * * *

SEQUENCE LISTING

```
<160> NUMBER OF SEQ ID NOS: 41

<210> SEQ ID NO 1
<211> LENGTH: 56
<212> TYPE: DNA
<213> ORGANISM: Artificial Sequence
<220> FEATURE:
<223> OTHER INFORMATION: Synthetic Primer A - forward primer

<400> SEQUENCE: 1
tttggcggcg gcggcgcatt ctgcctttgc gggagatagg gtggcagatg taattg        56

<210> SEQ ID NO 2
<211> LENGTH: 55
<212> TYPE: DNA
<213> ORGANISM: Artificial Sequence
<220> FEATURE:
<223> OTHER INFORMATION: Synthetic Primer B- reverse primer

<400> SEQUENCE: 2
catgatatgg caaaggaaat ccataggatc caaagagtgg tgatcgctgt gcgac         55
```

```
<210> SEQ ID NO 3
<211> LENGTH: 72
<212> TYPE: DNA
<213> ORGANISM: Artificial Sequence
<220> FEATURE:
<223> OTHER INFORMATION: Synthetic Primer C - reverse primer

<400> SEQUENCE: 3
ttggcaggcc cacatgatga accccaacaa agcaacacaa agcaaaaaac atgatatggc      60
aaaggaaatc ca                                                         72

<210> SEQ ID NO 4
<211> LENGTH: 61
<212> TYPE: DNA
<213> ORGANISM: Artificial Sequence
<220> FEATURE:
<223> OTHER INFORMATION: Synthetic Primer D - forward primer

<400> SEQUENCE: 4
aatcggtccg atggtaagcg ctattgtttt atatgtgctt ttggcggcgg ggcgcattct      60
g                                                                     61

<210> SEQ ID NO 5
<211> LENGTH: 53
<212> TYPE: DNA
<213> ORGANISM: Artificial Sequence
<220> FEATURE:
<223> OTHER INFORMATION: Synthetic Primer E - reverse primer

<400> SEQUENCE: 5
aataagcttt taatattgtc tattacggtt ttggcaggcc cacatgatga acc             53

<210> SEQ ID NO 6
<211> LENGTH: 32
<212> TYPE: DNA
<213> ORGANISM: Artificial Sequence
<220> FEATURE:
<223> OTHER INFORMATION: Synthetic Primer F - forward primer

<400> SEQUENCE: 6
cctacgtatc aattttatgt ggctaatgga ga                                   32

<210> SEQ ID NO 7
<211> LENGTH: 36
<212> TYPE: DNA
<213> ORGANISM: Artificial Sequence
<220> FEATURE:
<223> OTHER INFORMATION: Synthetic Primer G - reverse primer

<400> SEQUENCE: 7
cgcgtcgacc ttgagtggag agagagctag ttataa                               36

<210> SEQ ID NO 8
<211> LENGTH: 25
<212> TYPE: DNA
<213> ORGANISM: Artificial Sequence
<220> FEATURE:
<223> OTHER INFORMATION: A Synthetic Capsid 76 F - Forward primer

<400> SEQUENCE: 8
attaatgatt ttcttccccc aggag                                           25

<210> SEQ ID NO 9
<211> LENGTH: 30
```

```
<212> TYPE: DNA
<213> ORGANISM: Artificial Sequence
<220> FEATURE:
<223> OTHER INFORMATION: A Synthetic Capsid 135 R - Reverse primer

<400> SEQUENCE: 9
ggctgtggcc tttgttacaa agttatcatc                                    30

<210> SEQ ID NO 10
<211> LENGTH: 32
<212> TYPE: DNA
<213> ORGANISM: Artificial Sequence
<220> FEATURE:
<223> OTHER INFORMATION: A Synthetic Capsid 121 F - Forward primer

<400> SEQUENCE: 10
agtgctgtta ttctagatga taactttgta ac                                 32

<210> SEQ ID NO 11
<211> LENGTH: 35
<212> TYPE: DNA
<213> ORGANISM: Artificial Sequence
<220> FEATURE:
<223> OTHER INFORMATION: A Synthetic Capsid 180 R - Reverse primer

<400> SEQUENCE: 11
tcttttgttg tttggttgga agtaatcaat agtgg                              35

<210> SEQ ID NO 12
<211> LENGTH: 25
<212> TYPE: DNA
<213> ORGANISM: Artificial Sequence
<220> FEATURE:
<223> OTHER INFORMATION: A Synthetic ORF7 F - Forward primer

<400> SEQUENCE: 12
atgccaaata acaacggcaa gcagc                                         25

<210> SEQ ID NO 13
<211> LENGTH: 24
<212> TYPE: DNA
<213> ORGANISM: Artificial Sequence
<220> FEATURE:
<223> OTHER INFORMATION: A Synthetic ORF7 R - Reverse primer

<400> SEQUENCE: 13
tgctgagggt gatgctgtga cgcg                                          24

<210> SEQ ID NO 14
<211> LENGTH: 20
<212> TYPE: PRT
<213> ORGANISM: Enterovirus virus
<220> FEATURE:
<223> OTHER INFORMATION: 71
<220> FEATURE:
<221> NAME/KEY: SIGNAL
<222> LOCATION: (1)..(20)
<220> FEATURE:
<221> NAME/KEY: SIGNAL
<222> LOCATION: (1)..(20)
<223> OTHER INFORMATION: gp64 signal peptide sequence

<400> SEQUENCE: 14

Met Val Ser Ala Ile Val Leu Tyr Val Leu Leu Ala Ala Ala Ala His
1               5                   10                  15

Ser Ala Phe Ala
            20
```

```
<210> SEQ ID NO 15
<211> LENGTH: 7
<212> TYPE: PRT
<213> ORGANISM: Baculovirus
<220> FEATURE:
<221> NAME/KEY: DOMAIN
<222> LOCATION: (1)..(7)
<220> FEATURE:
<221> NAME/KEY: DOMAIN
<222> LOCATION: (1)..(7)
<223> OTHER INFORMATION: Full length sequence of gp64 cytoplasmic domain
      (CTD)

<400> SEQUENCE: 15

Arg Asn Arg Asn Arg Gln Tyr
1               5

<210> SEQ ID NO 16
<211> LENGTH: 6
<212> TYPE: PRT
<213> ORGANISM: Baculovirus
<220> FEATURE:
<221> NAME/KEY: Truncated sequence of gp64 cytoplasmic domain containing
      6 amino acids (CTD)
<222> LOCATION: (1)..(6)
<220> FEATURE:
<221> NAME/KEY: DOMAIN
<222> LOCATION: (1)..(6)

<400> SEQUENCE: 16

Asn Arg Asn Arg Gln Tyr
1               5

<210> SEQ ID NO 17
<211> LENGTH: 27
<212> TYPE: PRT
<213> ORGANISM: Influenza virus
<220> FEATURE:
<221> NAME/KEY: TRANSMEM
<222> LOCATION: (1)..(27)
<223> OTHER INFORMATION: Sequence of the H3N2-Ha transmembrane domain
<220> FEATURE:
<221> NAME/KEY: TRANSMEM
<222> LOCATION: (1)..(27)
<223> OTHER INFORMATION: Sequence of the H3N2-HA transmembrane domain

<400> SEQUENCE: 17

Trp Ile Leu Trp Ile Ser Phe Ala Ile Ser Cys Phe Leu Leu Cys Val
1               5                   10                  15

Ala Leu Leu Gly Phe Ile Met Trp Ala Cys Gln
            20                  25

<210> SEQ ID NO 18
<211> LENGTH: 501
<212> TYPE: DNA
<213> ORGANISM: baculovirus
<220> FEATURE:
<223> OTHER INFORMATION: white spot syndrome
<220> FEATURE:
<221> NAME/KEY: promoter
<222> LOCATION: (1)..(501)
<223> OTHER INFORMATION: Sequence of the White Spot Syndrome Virus ie1
      promoter

<400> SEQUENCE: 18
tcaattttat gtggctaatg gagaattgtc gtgccagttg tatcagcgaa gcggagatgt      60 cggggttgggc gtgcccttca atattgcatc atactctctt ctgactcatc tgatggccag   120
```

```
tatggtgggt ctaaaaccgg agagtttat cctcactctt ggtgacgcac acatttataa      180
tacccacatt gaggtgttaa agaagcagtt gtgccgcgtc cctagaccat tccctaagtt      240
gaggatttta atggctccag aaaaaattga ggactttact atcgacatgt tttatcttga      300
ggggtatcaa ccacacagtg gaaacttgca atgaaaatg gctgtttgaa tcatgttaag       360
gaatttcctt gttactcatt tattcctaga aatggtgtaa tcgctgttgt gggcggagca      420
tatttgtgta tataagagcc cgtgttagct cctcgattca gtcacaagag cgcacacaca      480
cgcttataac tagctctctc t                                                501
```

```
<210> SEQ ID NO 19
<211> LENGTH: 897
<212> TYPE: DNA
<213> ORGANISM: Enterovirus
<220> FEATURE:
<223> OTHER INFORMATION: 71
<220> FEATURE:
<221> NAME/KEY: gene
<222> LOCATION: (1)..(897)
<223> OTHER INFORMATION: Sequence of VP1 of EV71 virus

<400> SEQUENCE: 19
atgggagata gggtggcaga tgtaattgaa agttccatag agatagcgt gagcagagcc        60 ctcactcacg ctctaccagc acccacaggc cagaacacac aggtgagcag tcatcgactg      120
gatacaggca aggttccagc actccaagct gctgaaattg gagcatcatc aaatgctagt      180
gacgagagca tgattgagac acgctgtgtt cttaactcgc acagtacagc tgagaccact      240
cttgatagtt tcttcagcag ggcgggatta gttggagaga tagatctccc tcttgagggc      300
acaactaacc caaatggtta tgccaactgg gacatagata taacaggtta cgcgcaaatg      360
cgtagaaagg tagagctatt cacctacatg cgctttgatg cagagttcac ttttgttgcg      420
tgcacaccca ccggggaagt tgtcccacaa ttgctccaat atatgtttgt gccacctgga      480
gcccctaagc cagattctag ggaatccctt gcatggcaaa ccgccactaa cccctcagtt      540
tttgtcaagc tgtcagaccc tccagcgcag gtttcagtgc cattcatgtc acctgcgagt      600
gcttaccaat ggttttatga cggatatccc acattcggag aacacaaaca ggagaaagat      660
cttgaatacg gggcatgtcc taataacatg atgggcacgt tctcagtgcg gactgtgggg      720
acctccaagt ccaagtaccc tttagtggtt aggatttaca tgagaatgaa gcacgtcagg      780
gcgtggatac ctcgcccgat gcgtaaccag aactacctat tcaaagccaa cccaaattat      840
gctggcaact ccattaagcc aactggtgcc agtcgcacag cgatcaccac tctttaa         897
```

```
<210> SEQ ID NO 20
<211> LENGTH: 702
<212> TYPE: DNA
<213> ORGANISM: Porcine circovirus
<220> FEATURE:
<221> NAME/KEY: Sequence of PCV2 capsid protein
<222> LOCATION: (1)..(702)

<400> SEQUENCE: 20
atgacgtatc caaggaggcg ttaccggaga agaagacacc gccccgcag ccatcttggc         60 cagatcctcc gccgccgccc ctggctcgtc caccccgcc accgttaccg ctggagaagg       120
aaaaatggca tcttcaacac ccgcctctcc cgcaccttcg atatactat caagcgaacc       180 acagtcaaaa cgccctcttg gcggtggac atgatgagat tcaatattaa tgattttctt       240
cccccaggag ggggctcaaa ccccgctct gtgcccttg aatactacag aataagaaag      300
```

```
gttaaggttg aattctggcc ctgctccccg atcacccagg gtgacagggg agtgggctcc    360
agtgctgtta ttctagatga taactttgta acaaaggcca cagccctcac ctatgacccc    420
tatgtaaact actcctcccg ccataccata acccagccct tctcctacca ctcccgctac    480
tttaccccca aacctgtcct agattccact attgattact tccaaccaaa caacaaaaga    540
aatcagctgt ggctgagact acaaactgct ggaaatgtag accacgtagg cctcggcact    600
gcgttcgaaa acagtatata cgaccaggaa tacaatatcc gtgtaaccat gtatgtacaa    660
ttcagagaat ttaatcttaa agaccccccca cttaacccct aa                       702

<210> SEQ ID NO 21
<211> LENGTH: 372
<212> TYPE: DNA
<213> ORGANISM: Porcine virus
<220> FEATURE:
<223> OTHER INFORMATION: reproductive and respiratory syndrome virus
<220> FEATURE:
<221> NAME/KEY: gene
<222> LOCATION: (1)..(372)
<223> OTHER INFORMATION: Sequence of ORF7 of PRRSV capsid protein

<400> SEQUENCE: 21
atgccaaata caacggcaa gcagcagaag agaaagaagg gggatggcca gccagtcaat     60
cagctgtgcc agatgctggg taagatcatc gctcagcaaa accagtccag aggcaaggga    120
ccgggaaaga aaataagaa gaaaaacccg gagaagcccc attttcctct agcgactgaa     180
gatgatgtca gacatcactt tacccccagt gagcggcaat tgtgtctgtc gtcaatccag    240
accgccttta tcaaggcgc tgggacttgc accctgtcag attcagggag ataagttac     300 actgtggagt ttagtttgcc tacgcatcat actgtgcgcc tgatccgcgt cacagcatca    360
ccctcagcat ga                                                       372

<210> SEQ ID NO 22
<211> LENGTH: 1017
<212> TYPE: DNA
<213> ORGANISM: Fish nodavirus
<220> FEATURE:
<221> NAME/KEY: gene
<222> LOCATION: (1)..(1017)
<223> OTHER INFORMATION: Sequence of fish nodavirus capsid protein alpha

<400> SEQUENCE: 22
atggtacgca aaggtgagaa gaaattggca aaacccgcga ccaccaaggc cgcgaatccg     60 caacccccgcc gacgtgctaa caatcgtcgg cgtagtaatc gcactgacgc acctgtgtct    120
aaggcctcga ctgtaactgg attcggacgt gggaccaatg acgtccatct ctcaggtatg    180
tcgagaatct cccaggccgt cctcccagcc gggacaggaa cagacggata cgttgttgtt    240
gacgcaacca tcgtccccga cctcctgcca cgactgggac acgctgctag aatcttccag    300
cgatacgctg ttgaaacact ggagtttgaa attcagccaa tgtgcccgc aaacacgggc     360 ggtggttacg ttgctggctt cctgcctgat ccaactgaca cgatcacac cttcgacgcg    420 cttcaagcaa ctcgtggtgc agtcgttgcc aaatggtggg aaagcagaac agtccgacct    480
cagtacaccc gcacgctcct ctggacctcg tcgggaaagg agcagcgtct cacgtcacct    540
ggtcggctga tactcctgtg tgtcggcaac aacactgatg tggtcaacgt gtcagtgctg    600
tgtcgctgga gtgttcgact gagcgttcca tctcttgaga cacctgaaga gaccaccgct    660
cccatcatga cacaaggttc cctgtacaac gattccctt ccacaaatga cttcaagtcc     720
atcctcctag gatccacacc actggacatt gcccctgatg gagcagtctt ccagctggac    780
```

```
cgtccgctgt ccattgacta catccttgga actggagatg ttgaccgtgc tgtttattgg      840
caccttaaga agtttgctgg aaatgctggc acacctgcag gctggtttcg ctggggcatc      900
tgggacaact ttaataagac gttcacagat ggcgttgctt actactctga tgagcagccc      960
cgtcaaatcc tgctgcctgt tggcactgtc tgcaccaggg ttgactcggg aaactaa       1017
```

```
<210> SEQ ID NO 23
<211> LENGTH: 12
<212> TYPE: PRT
<213> ORGANISM: Enterovirus
<220> FEATURE:
<223> OTHER INFORMATION: 71
<220> FEATURE:
<221> NAME/KEY: MISC_FEATURE
<223> OTHER INFORMATION: EV71 - VP1 - 167th to 178th amino acids

<400> SEQUENCE: 23

Arg Glu Ser Leu Ala Trp Gln Thr Ala Thr Asn Pro
1               5                   10

<210> SEQ ID NO 24
<211> LENGTH: 14
<212> TYPE: PRT
<213> ORGANISM: Enterovirus
<220> FEATURE:
<223> OTHER INFORMATION: 71
<220> FEATURE:
<221> NAME/KEY: MISC_FEATURE
<222> LOCATION: (1)..(14)
<223> OTHER INFORMATION: EV71 - VP1 - 209th to 222nd amino acids

<400> SEQUENCE: 24

Tyr Pro Thr Phe Gly Glu His Lys Gln Glu Lys Asp Leu Glu
1               5                   10

<210> SEQ ID NO 25
<211> LENGTH: 21
<212> TYPE: PRT
<213> ORGANISM: Enterovirus
<220> FEATURE:
<223> OTHER INFORMATION: 71
<220> FEATURE:
<221> NAME/KEY: MISC_FEATURE
<222> LOCATION: (1)..(21)
<223> OTHER INFORMATION: EV71 - VP1 - 240th to 260th amino acids

<400> SEQUENCE: 25

Gly Ser Ser Lys Ser Lys Tyr Pro Leu Val Val Arg Ile Tyr Met Arg
1               5                   10                  15

Met Lys His Val Arg
            20

<210> SEQ ID NO 26
<211> LENGTH: 51
<212> TYPE: PRT
<213> ORGANISM: Porcine circovirus
<220> FEATURE:
<221> NAME/KEY: MISC_FEATURE
<222> LOCATION: (1)..(51)
<223> OTHER INFORMATION: PCV2 - ORF2 - 100th to 150th amino acids

<400> SEQUENCE: 26

Lys Val Lys Val Glu Phe Trp Pro Cys Ser Pro Ile Thr Gln Gly Asp
1               5                   10                  15

Arg Gly Val Gly Ser Ser Ala Val Ile Leu Asp Asp Asn Phe Val Thr
            20                  25                  30
```

```
Lys Ala Thr Ala Leu Thr Tyr Asp Pro Tyr Val Asn Tyr Ser Ser Arg
        35                  40                  45

His Thr Ile
        50

<210> SEQ ID NO 27
<211> LENGTH: 50
<212> TYPE: PRT
<213> ORGANISM: Porcine circovirus

<400> SEQUENCE: 27

Thr Gln Pro Phe Ser Tyr His Ser Arg Tyr Phe Thr Pro Lys Pro Val
1               5                   10                  15

Leu Asp Ser Thr Ile Asp Tyr Phe Gln Pro Asn Asn Lys Arg Asn Gln
            20                  25                  30

Leu Trp Leu Arg Leu Gln Thr Ala Gly Asn Val Asp His Val Gly Leu
        35                  40                  45

Gly Thr
    50

<210> SEQ ID NO 28
<211> LENGTH: 40
<212> TYPE: PRT
<213> ORGANISM: Porcine virus
<220> FEATURE:
<223> OTHER INFORMATION: reproductive and respiratory syndrome virus
<220> FEATURE:
<221> NAME/KEY: MISC_FEATURE
<222> LOCATION: (1)..(40)
<223> OTHER INFORMATION: PRRSV - ORF7 - 18th to 57th amino aicds

<400> SEQUENCE: 28

Pro Val Asn Gln Leu Cys Gln Met Leu Gly Lys Ile Ile Ala Gln Gln
1               5                   10                  15

Asn Gln Ser Arg Gly Lys Gly Pro Gly Lys Lys Asn Lys Lys Lys Asn
            20                  25                  30

Pro Glu Lys Pro His Phe Pro Leu
        35                  40

<210> SEQ ID NO 29
<211> LENGTH: 66
<212> TYPE: PRT
<213> ORGANISM: Porcine virus
<220> FEATURE:
<223> OTHER INFORMATION: reproductive and respiratory syndrome virus
<220> FEATURE:
<221> NAME/KEY: MISC_FEATURE
<222> LOCATION: (1)..(66)
<223> OTHER INFORMATION: PRRSV - ORF7 - 58th to 123rd amino acids

<400> SEQUENCE: 29

Ala Thr Glu Asp Asp Val Arg His His Phe Thr Pro Ser Glu Arg Gln
1               5                   10                  15

Leu Cys Leu Ser Ser Ile Gln Thr Ala Phe Asn Gln Gly Ala Gly Thr
            20                  25                  30

Cys Thr Leu Ser Asp Ser Gly Arg Ile Ser Tyr Thr Val Glu Phe Ser
        35                  40                  45

Leu Pro Thr His His Thr Val Arg Leu Ile Arg Val Thr Ala Ser Pro
    50                  55                  60

Ser Ala
65
```

<210> SEQ ID NO 30
<211> LENGTH: 38
<212> TYPE: PRT
<213> ORGANISM: Porcine virus
<220> FEATURE:
<223> OTHER INFORMATION: reproductive and respiratory syndrome virus
<220> FEATURE:
<221> NAME/KEY: MISC_FEATURE
<222> LOCATION: (1)..(38)
<223> OTHER INFORMATION: PRRSV - ORF5 - 28th to 65th amino acids

<400> SEQUENCE: 30

```
Leu Ala Asn Ala Ser Asn Ser Ser Ser His Leu Gln Leu Ile Tyr
1               5                   10                  15

Asn Leu Thr Leu Cys Glu Leu Asn Gly Thr Asp Trp Leu Ala Asn Arg
            20                  25                  30

Phe Asp Trp Ala Val Glu
        35
```

<210> SEQ ID NO 31
<211> LENGTH: 69
<212> TYPE: PRT
<213> ORGANISM: Porcine virus
<220> FEATURE:
<223> OTHER INFORMATION: reproductive and respiratory syndrome virus
<220> FEATURE:
<221> NAME/KEY: MISC_FEATURE
<222> LOCATION: (1)..(69)
<223> OTHER INFORMATION: PRRSV - ORF5 - 132nd to 200th amino acids

<400> SEQUENCE: 31

```
Met Ser Trp Arg Tyr Ala Cys Thr Arg Tyr Thr Asn Phe Leu Leu Asp
1               5                   10                  15

Thr Lys Gly Arg Leu Tyr Arg Trp Arg Ser Pro Val Ile Ile Glu Lys
            20                  25                  30

Arg Gly Lys Val Glu Val Glu Gly His Leu Ile Asp Leu Lys Arg Val
        35                  40                  45

Val Leu Asp Gly Ser Val Ala Thr Pro Ile Thr Arg Val Ser Ala Glu
    50                  55                  60

Gln Trp Gly Arg Pro
65
```

<210> SEQ ID NO 32
<211> LENGTH: 107
<212> TYPE: PRT
<213> ORGANISM: Porcine virus
<220> FEATURE:
<223> OTHER INFORMATION: reproductive and respiratory syndrome virus
<220> FEATURE:
<221> NAME/KEY: MISC_FEATURE
<222> LOCATION: (1)..(107)
<223> OTHER INFORMATION: PRRSV - ORF5 - combination of 28th to 65th and
     13nd to 200th amino acids

<400> SEQUENCE: 32

```
Leu Ala Asn Ala Ser Asn Ser Ser Ser His Leu Gln Leu Ile Tyr
1               5                   10                  15

Asn Leu Thr Leu Cys Glu Leu Asn Gly Thr Asp Trp Leu Ala Asn Arg
            20                  25                  30

Phe Asp Trp Ala Val Glu Met Ser Trp Arg Tyr Ala Cys Thr Arg Tyr
        35                  40                  45

Thr Asn Phe Leu Leu Asp Thr Lys Gly Arg Leu Tyr Arg Trp Arg Ser
    50                  55                  60
```

```
Pro Val Ile Ile Glu Lys Arg Gly Lys Val Glu Val Gly His Leu
65                  70                  75                  80

Ile Asp Leu Lys Arg Val Val Leu Asp Gly Ser Val Ala Thr Pro Ile
                85                  90                  95

Thr Arg Val Ser Ala Glu Gln Trp Gly Arg Pro
            100                 105
```

<210> SEQ ID NO 33
<211> LENGTH: 298
<212> TYPE: PRT
<213> ORGANISM: Enterovirus
<220> FEATURE:
<223> OTHER INFORMATION: 71
<220> FEATURE:
<221> NAME/KEY: MISC_FEATURE
<222> LOCATION: (1)..(298)
<223> OTHER INFORMATION: Amino Acid Sequence of VP1 of EV71 virus
      corresponding to nucleic acid sequence SEQ ID NO:19, EV71-VP1

<400> SEQUENCE: 33

```
Met Gly Asp Arg Val Ala Asp Val Ile Glu Ser Ser Ile Gly Asp Ser
1               5                   10                  15

Val Ser Arg Ala Leu Thr His Ala Leu Pro Ala Pro Thr Gly Gln Asn
                20                  25                  30

Thr Gln Val Ser Ser His Arg Leu Asp Thr Gly Lys Val Pro Ala Leu
            35                  40                  45

Gln Ala Ala Glu Ile Gly Ala Ser Ser Asn Ala Ser Asp Glu Ser Met
    50                  55                  60

Ile Glu Thr Arg Cys Val Leu Asn Ser His Ser Thr Ala Glu Thr Thr
65                  70                  75                  80

Leu Asp Ser Phe Phe Ser Arg Ala Gly Leu Val Gly Glu Ile Asp Leu
                85                  90                  95

Pro Leu Glu Gly Thr Thr Asn Pro Asn Gly Tyr Ala Asn Trp Asp Ile
            100                 105                 110

Asp Ile Thr Gly Tyr Ala Gln Met Arg Arg Lys Val Glu Leu Phe Thr
        115                 120                 125

Tyr Met Arg Phe Asp Ala Glu Phe Thr Phe Val Ala Cys Thr Pro Thr
130                 135                 140

Gly Glu Val Val Pro Gln Leu Leu Gln Tyr Met Phe Val Pro Pro Gly
145                 150                 155                 160

Ala Pro Lys Pro Asp Ser Arg Glu Ser Leu Ala Trp Gln Thr Ala Thr
                165                 170                 175

Asn Pro Ser Val Phe Val Lys Leu Ser Asp Pro Pro Ala Gln Val Ser
            180                 185                 190

Val Pro Phe Met Ser Pro Ala Ser Ala Tyr Gln Trp Phe Tyr Asp Gly
        195                 200                 205

Tyr Pro Thr Phe Gly Glu His Lys Gln Glu Lys Asp Leu Glu Tyr Gly
    210                 215                 220

Ala Cys Pro Asn Asn Met Met Gly Thr Phe Ser Val Arg Thr Val Gly
225                 230                 235                 240

Thr Ser Lys Ser Lys Tyr Pro Leu Val Val Arg Ile Tyr Met Arg Met
                245                 250                 255

Lys His Val Arg Ala Trp Ile Pro Arg Pro Met Arg Asn Gln Asn Tyr
            260                 265                 270

Leu Phe Lys Ala Asn Pro Asn Tyr Ala Gly Asn Ser Ile Lys Pro Thr
        275                 280                 285

Gly Ala Ser Arg Thr Ala Ile Thr Thr Leu
```

290            295

<210> SEQ ID NO 34
<211> LENGTH: 233
<212> TYPE: PRT
<213> ORGANISM: Porcine circovirus
<220> FEATURE:
<221> NAME/KEY: MISC_FEATURE
<222> LOCATION: (1)..(233)
<223> OTHER INFORMATION: Amino Acid Sequence of PCV2 capsid protein
      corresponding to nucleic acid sequence SEQ ID NO: 20, Sequence
      of PCV2 capsid protein- PCV2 PRF2

<400> SEQUENCE: 34

Met Thr Tyr Pro Arg Arg Arg Tyr Arg Arg Arg His Arg Pro Arg
1               5                   10                  15

Ser His Leu Gly Gln Ile Leu Arg Arg Arg Pro Trp Leu Val His Pro
                20                  25                  30

Arg His Arg Tyr Arg Trp Arg Arg Lys Asn Gly Ile Phe Asn Thr Arg
            35                  40                  45

Leu Ser Arg Thr Phe Gly Tyr Thr Ile Lys Arg Thr Thr Val Lys Thr
        50                  55                  60

Pro Ser Trp Ala Val Asp Met Met Arg Phe Asn Ile Asn Asp Phe Leu
65                  70                  75                  80

Pro Pro Gly Gly Gly Ser Asn Pro Arg Ser Val Pro Phe Glu Tyr Tyr
                85                  90                  95

Arg Ile Arg Lys Val Lys Val Glu Phe Trp Pro Cys Ser Pro Ile Thr
            100                 105                 110

Gln Gly Asp Arg Gly Val Gly Ser Ser Ala Val Ile Leu Asp Asp Asn
        115                 120                 125

Phe Val Thr Lys Ala Thr Ala Leu Thr Tyr Asp Pro Tyr Val Asn Tyr
    130                 135                 140

Ser Ser Arg His Thr Ile Thr Gln Pro Phe Ser Tyr His Ser Arg Tyr
145                 150                 155                 160

Phe Thr Pro Lys Pro Val Leu Asp Ser Thr Ile Asp Tyr Phe Gln Pro
                165                 170                 175

Asn Asn Lys Arg Asn Gln Leu Trp Leu Arg Leu Gln Thr Ala Gly Asn
            180                 185                 190

Val Asp His Val Gly Leu Gly Thr Ala Phe Glu Asn Ser Ile Tyr Asp
        195                 200                 205

Gln Glu Tyr Asn Ile Arg Val Thr Met Tyr Val Gln Phe Arg Glu Phe
    210                 215                 220

Asn Leu Lys Asp Pro Pro Leu Asn Pro
225                 230

<210> SEQ ID NO 35
<211> LENGTH: 123
<212> TYPE: PRT
<213> ORGANISM: Porcine virus
<220> FEATURE:
<223> OTHER INFORMATION: reproductive and respiratory syndrome virus
<220> FEATURE:
<221> NAME/KEY: MISC_FEATURE
<222> LOCATION: (1)..(123)
<223> OTHER INFORMATION: Amino Acid Sequence of ORF7 of PRRSV capsid
      protein corresponding to nucleic acid sequence SEQ ID NO: 21,
      Sequence of ORF7 of PRRSV capsid protein- PRRSV ORF7

<400> SEQUENCE: 35

Met Pro Asn Asn Asn Gly Lys Gln Gln Lys Arg Lys Lys Gly Asp Gly
1               5                   10                  15

```
Gln Pro Val Asn Gln Leu Cys Gln Met Leu Gly Lys Ile Ile Ala Gln
             20                  25                  30

Gln Asn Gln Ser Arg Gly Lys Gly Pro Gly Lys Lys Asn Lys Lys Lys
         35                  40                  45

Asn Pro Glu Lys Pro His Phe Pro Leu Ala Thr Glu Asp Asp Val Arg
 50                      55                  60

His His Phe Thr Pro Ser Glu Arg Gln Leu Cys Leu Ser Ser Ile Gln
 65                  70                  75                  80

Thr Ala Phe Asn Gln Gly Ala Gly Thr Cys Thr Leu Ser Asp Ser Gly
                 85                  90                  95

Arg Ile Ser Tyr Thr Val Glu Phe Ser Leu Pro Thr His His Thr Val
             100                 105                 110

Arg Leu Ile Arg Val Thr Ala Ser Pro Ser Ala
         115                 120
```

<210> SEQ ID NO 36
<211> LENGTH: 338
<212> TYPE: PRT
<213> ORGANISM: Fish nodavirus
<220> FEATURE:
<221> NAME/KEY: MISC_FEATURE
<222> LOCATION: (1)..(338)
<223> OTHER INFORMATION: Amino Acid Sequence of fish nodavirus capsid
      protein corresponding to nucleic acid sequence SEQ ID NO:22:
      Sequence of fish nodavirus capsid protein- Capsid protein Alpha

<400> SEQUENCE: 36

```
Met Val Arg Lys Gly Glu Lys Lys Leu Ala Lys Pro Ala Thr Thr Lys
 1               5                  10                  15

Ala Ala Asn Pro Gln Pro Arg Arg Arg Ala Asn Asn Arg Arg Arg Ser
             20                  25                  30

Asn Arg Thr Asp Ala Pro Val Ser Lys Ala Ser Thr Val Thr Gly Phe
         35                  40                  45

Gly Arg Gly Thr Asn Asp Val His Leu Ser Gly Met Ser Arg Ile Ser
     50                  55                  60

Gln Ala Val Leu Pro Ala Gly Thr Gly Thr Asp Gly Tyr Val Val Val
 65                  70                  75                  80

Asp Ala Thr Ile Val Pro Asp Leu Leu Pro Arg Leu Gly His Ala Ala
                 85                  90                  95

Arg Ile Phe Gln Arg Tyr Ala Val Glu Thr Leu Glu Phe Glu Ile Gln
             100                 105                 110

Pro Met Cys Pro Ala Asn Thr Gly Gly Gly Tyr Val Ala Gly Phe Leu
         115                 120                 125

Pro Asp Pro Thr Asp Asn Asp His Thr Phe Asp Ala Leu Gln Ala Thr
 130                 135                 140

Arg Gly Ala Val Val Ala Lys Trp Trp Glu Ser Arg Thr Val Arg Pro
145                 150                 155                 160

Gln Tyr Thr Arg Thr Leu Leu Trp Thr Ser Ser Gly Lys Glu Gln Arg
                 165                 170                 175

Leu Thr Ser Pro Gly Arg Leu Ile Leu Leu Cys Val Gly Asn Asn Thr
             180                 185                 190

Asp Val Val Asn Val Ser Val Leu Cys Arg Trp Ser Val Arg Leu Ser
         195                 200                 205

Val Pro Ser Leu Glu Thr Pro Glu Glu Thr Thr Ala Pro Ile Met Thr
     210                 215                 220

Gln Gly Ser Leu Tyr Asn Asp Ser Leu Ser Thr Asn Asp Phe Lys Ser
```

```
                225                 230                 235                 240

Ile Leu Leu Gly Ser Thr Pro Leu Asp Ile Ala Pro Asp Gly Ala Val
                245                 250                 255

Phe Gln Leu Asp Arg Pro Leu Ser Ile Asp Tyr Ile Leu Gly Thr Gly
                260                 265                 270

Asp Val Asp Arg Ala Val Tyr Trp His Leu Lys Lys Phe Ala Gly Asn
                275                 280                 285

Ala Gly Thr Pro Ala Gly Trp Phe Arg Trp Gly Ile Trp Asp Asn Phe
            290                 295                 300

Asn Lys Thr Phe Thr Asp Gly Val Ala Tyr Tyr Ser Asp Glu Gln Pro
305                 310                 315                 320

Arg Gln Ile Leu Leu Pro Val Gly Thr Val Cys Thr Arg Val Asp Ser
                325                 330                 335

Gly Asn
```

<210> SEQ ID NO 37
<211> LENGTH: 95
<212> TYPE: DNA
<213> ORGANISM: Artificial Sequence
<220> FEATURE:
<223> OTHER INFORMATION: A synthetic Noda F - Forward primer

<400> SEQUENCE: 37

```
aatcggtccg atggtaagcg ctattgtttt atatgtgctt ttggcggcgg cggcgcattc    60
tgcctttgcg gtacgcaaag gtgagaagaa attgg                              95
```

<210> SEQ ID NO 38
<211> LENGTH: 50
<212> TYPE: DNA
<213> ORGANISM: Artificial Sequence
<220> FEATURE:
<223> OTHER INFORMATION: A synthetic NodaR1 - Reverse Primer

<400> SEQUENCE: 38

```
tggcaaagga aatccatagg atccagtttc ccgagtcaac cctggtgcag              50
```

<210> SEQ ID NO 39
<211> LENGTH: 107
<212> TYPE: DNA
<213> ORGANISM: Artificial Sequence
<220> FEATURE:
<223> OTHER INFORMATION: A synthetic NodaR2 - Reverse Primer

<400> SEQUENCE: 39

```
aagcttattt taatattgtc tattacggtt ttggcaggcc cacatgatga accccaacaa    60
agcaacacaa agcaaaaaac atgatatggc aaaggaaatc catagga                 107
```

<210> SEQ ID NO 40
<211> LENGTH: 18
<212> TYPE: DNA
<213> ORGANISM: Artificial Sequence
<220> FEATURE:
<223> OTHER INFORMATION: A synthetic UTR-F - Forward Primer

<400> SEQUENCE: 40

```
tcctccggcc cctgaatg                                                 18
```

<210> SEQ ID NO 41
<211> LENGTH: 22
<212> TYPE: DNA
<213> ORGANISM: Artificial Sequence -continued

```
<220> FEATURE:
<223> OTHER INFORMATION: A synthetic UTR-R - Reverse Primer

<400> SEQUENCE: 41
ggacacccaa agtagtcggt tc                                               22
```